US008399447B2

(12) United States Patent
Pervaiz et al.

(10) Patent No.: US 8,399,447 B2
(45) Date of Patent: Mar. 19, 2013

(54) METAL TRIANGULO COMPOUND AND METHODS OF USING THE SAME

(75) Inventors: Shazib Pervaiz, Singapore (SG); Sanjiv Kumar Yadav, Singapore (SG)

(73) Assignee: National University of Singapore, Singapore (SG)

( * ) Notice: Subject to any disclaimer, the term of this patent is extended or adjusted under 35 U.S.C. 154(b) by 471 days.

(21) Appl. No.: 12/596,138

(22) PCT Filed: Apr. 4, 2008

(86) PCT No.: PCT/SG2008/000110
§ 371 (c)(1),
(2), (4) Date: Apr. 20, 2010

(87) PCT Pub. No.: WO2008/127197
PCT Pub. Date: Oct. 23, 2008

(65) Prior Publication Data
US 2010/0209431 A1    Aug. 19, 2010

Related U.S. Application Data

(60) Provisional application No. 60/912,042, filed on Apr. 16, 2007.

(51) Int. Cl.
*A61K 31/555* (2006.01)
*C07D 215/16* (2006.01)
(52) U.S. Cl. .............................. 514/187; 546/7; 546/10
(58) Field of Classification Search .................. 514/187; 546/7, 10
See application file for complete search history.

(56) References Cited

PUBLICATIONS

Adams et al, Promotion of ring-opening nucleophilic addition to thietane ligands by the bridging coordination of the sulfur atom in the osmium cluster complexes Os3(CO)10[.mu.-[cyclic]SCH2CMe2CH2] and Os3(CO)10[.mu.-trans-[cyclic]SC(H)MeCH2C(H)Me], Organometallics, (1992), 11:1460-1465.
Ahmad et al, Hydrogen peroxide-mediated cytosolic acidification is a signal for mitochondrial transiocation of Bax during drug-induced apoptosis of tumor cells, Cancer Research, (2004) 64:7867-7878.
Ahmed et al, Colloidal silver nanoparticles stabilized by a water-soluble triosmium cluster, Journal of Organometallic Chemistry (2006), 691:1055-1060.
Ahmed et al, Luminescent silver nanoparticles stabilised by a crown ether capped with an organometallic cluster, Journal of Organometallic Chemistry (2007), 692:3474-3478.
Aliardyce et al, Development of organometallic (organo-transition metal) pharmaceuticals, Applied Organometallic Chemistry (2005), 19:1-10.
Azam et al, Triosmium and triruthenium clusters containing deprotanated 2-mercapto-1-methylimidazole ligand: X-ray structures of [(μ-H)Os$_3$(CO)$_{10}${ μ-SC=NCH=CHN(CH$_3$)}], [(μ-H)Ru$_3$(CO)$_3$ {(μ$_3$-n$^2$-SC=NCH=CHN(CH$_3$)}] and [(μ-H)Os$_3$(CO)$_8${μ-SC=NCH=CHN(CH$_3$)}( μ-dppm)}], Polyhedron, 21:885-892, 2002.
Azam et at, Metallation of Hydroxy-aryl and -alkyl Compounds by Reaction with Dodecacarbonyl-*triangulo*-triosmium, J.C.S. Dalton (1976), 1853-1858.
Brodie et al., The Reaction of [Os$_3$(CO)$_{10}$(MeCN)$_2$] with Heterocyclic Thioamides. The Crystal and Molecular Structure of [OS$_3$(μ-H)(CO)$_{10}${μ-SC=NCH$_2$CH$_2$S)], J. Chem. Soc. Dalton Trans, (1986), p. 633-639.
Cabeza et al, Triruthenium, Hexaruthenium, and Triosmium Carbonyl Derivatives of 2-Amino-6-phenylpyridine, Organometallics (2004), 23:1107-1115.
Choucroun et al, Comet assay and early apoptosis, Mutat. Res., (2001), 478:89-96.
Colangelo et al, Water-soluble benzoheterocycle triosmium clusters as potential inhibitors of telomerase enzyme, Journal of Inorganic Biochemistry (2005), 99:505-512.
Hanif et al, Dithiolate complexes of ruthenium and osmium: X-ray structures of [Ru$_2$(CO)$_6$(μ-SCH$_2$CH$_2$S)] and [{(μ-H)M$_3$(CO)$_{10}$) }$_2$(μ-SCH$_2$CH$_2$CH$_2$S)](M=Ru, Os), Polyhedron, (2000), 19:1073-1080.
Hirpara et al, Intracellular acidification triggered by mitochondrial-derived hydrogen peroxide is an effector mechanism for drug-induced apoptosis in tumor cells, J. Biol. Chem., (2001), 276(1):514-521.
Hung et al, Reactions of 1-Hydroxypyridine-2-thione with Triosmium Clusters. Preparation and Transformation of N-Oxide-Containing Osmium Complexes, Organometallics, (1996), 15:5605-5612.
International Preliminary Report on Patentability dated May 19, 2009 for PCT Application No. PCT/SG2008/000110.
International Search Report and the Written Opinion dated Jun. 20, 2009 for PCT Application No. PCT/SG2008/000110.
Jeannin et al, Structural Study of Transition-Metal Hydride Complexes in Relation to Corrosion Inhibition: Crystal and Molecular Structures of RU$_3$H(CO)$_{10}$(SCH$_2$COOH) and RU$_3$H(CO)$_9$(C$_7$H$_4$NS$_2$), Inorganic Chemistry, (1978), 17(8):2103-2110.
Johnson et al, Systematic synthesis of substituted hexanuclea phophide- andphophinidene-bridged osmium clusters, J. Chem. Soc. Dalton Trans., (1996), p. 755-763.
Kabir et al, Abstract—Synthesis and Reactivity of [(μ-H)OS3(CO)10(cyclic)( μ-SC:NCH:CHN(CH3)}], Journal of Bangladesh Academy of Sciences (2002), 26(2):135-141.
Lau et al, Synthesis of [{OS$_3$(CO)$_{10}$(μ$_2$-H)}$_2${μ$_2$,μ$_2$-NC$_6$H$_4$C$_6$H$_4$N}]and [{Os$_3$(CO)$_9$(μ$_2$-H)PPh$_3$)$_2$(μ$_2$, μ$_2$-NC$_5$H$_4$C$_6$H$_4$N}]; Carbon-carbon bond formation promoted by organorhodium species, Inorganica Chimica Acta (2006), 359:3632-3638.
Lee et al., Triosmium Carbonyl Clusters of Sulfur and Oxygen Mixed Donor Logands, Journal of Cluster Science, (1996), 7(3):435-453.
Mastrangelo et al, Polycyclic Aromatic Hydrocarbons and Cancer in Man, Environmental Health Perspective, (1996), vol. 104, No. 11, http://ehponline.org/members/1996/104-11/mastrangelo.html.
Melendez-Colon et al, Cancer initiation by polycyclic aromatic hydrocarbons results from formation of stable DNA adducts rather than apurinic sites, Carcinogenesis., (1999), 20(10):1885-1891.

(Continued)

*Primary Examiner* — Charanjit Aulakh
(74) *Attorney, Agent, or Firm* — Foley & Lardner LLP

(57) ABSTRACT

The present invention relates to metal triangulo compounds. Provided herein are also methods of inducing apoptosis in a cell that comprise administering a metal triangulo compound and methods of preventing carcinogenesis in a cell that comprise administering a metal triangulo compound.

10 Claims, 13 Drawing Sheets

PUBLICATIONS

Natarajan et al, Syntheses and Characterisation of $[Os_3(CO)_{11}(PRH_2)]$, $[(\mu_2\text{-H})Os_3(CO)_{10}(\mu_2\text{-PRH})]$ ($R=C_6H_5$,$\rho$-$CH_3OC_6H_4$, $C_6H_{11}$) and $[(\mu_2\text{-H})_2Os_3(CO)_9(\mu_3\text{-PR})]$ ($R=C_5H_5$, $C_5H_{11}$), Interconversion of Cluster-Bound Phosphine and Phosphido Ligands. Crystal and Molecular Structures of $[(\mu_2\text{-H})Os_3(CO)_{10}(\mu_2\text{-}P(C_6H_5)H)]$ and $[(\mu_2\text{-H})_2Os_3(CO)_9(\mu_3\text{-PC}_6H_5)]$, J. of Organometallic Chemistry, (1981), 220:365-381.

Pervaiz et al. Purified photoproducts of merocyanine 540 trigger cytochrome C release and caspase 8-dependent apoptosis in human leukemia and melanoma cells, Blood, (1999), 93(12):4096-4108.

Peter et al, Does CD95 have tumor promoting activities?, Biochimica et Biophysica Acta, (2005), 1755:25-36.

Poh et al, LY294002 and LY303511 sensitize tumor cells to drug-induced apoptosis via intracellular hydrogen peroxide production independent of the phosphoinositide 3-kinase-Akt pathway, Cancer Res., (2005), 65(14):6264-6274.

Potemkin et al., Abstract—Conformational States of Triosmium Clusters with Aminoacid Ligands: A Theoretical Study, Journal of Structural Chemistry (2003), 44(5):741-747.

Robey et al, Mitochondrial hexokinases, novel mediators of the antiapoptotic effects of growth factors and Akt, Oncogene, (2006), 25:4683-4696.

Rosenberg et al, Selective covalent binding of a positively charged water-soluble benzoheterocycle triosmium cluster to single- and double-stranded DNA, J. of Organometallic Chemistry, (2004), 689:4729-4735.

Rosenberg et al, Synthesis, characterization and DNA binding affinities of water-soluble benzoheterocycle trosmium clusters, Journal of Organometallic Chemistry, (2003), 668:51-58.

Rybicki et al, Polycyclic aromatic hydrocarbon-DNA adduct formation in prostate carcinogenesis, Cancer Letters, (2006), 239:157-167.

Samraj et al. Loss of caspase-9 provides genetic evidence for the type I/II concept of CD95-mediated apoptosis, J Biol Chem., (2006), 281(40):29652-29659.

Smith et al., Reativity of Electron-Deficient Benzoheterooyde Triosmium Clusters. 5. The Chemistry of $OS_3(CO)_8(\mu_3\text{-n}^2\text{-}(C(9)\text{—}N)\text{-}5,6\text{-benzoquinolyl})$ ($\mu$-H) and Its Phosphine Derivative, Organometallics, (1999), 18:3519-3527.

Wang et al, Caspase-10 is an initiator caspase in death receptor signaling, PNAS, (2001), 98(24):13884-13888.

Adam-Vizi et al. Bioenergetics and the formation of mitochodrial reactive oxygen species, Trends Pharmacol Sci, (2006), 27(12):639-645.

Borosky GL, Theoretical study related to the carcinogenic activity of polycyclic aromatic hydrocarbon derivatives, J Org Chem, (1999), (64):7738-7744.

Johnson et al, Dodecacarbonyltriruthenium and -triosmium, Inorganic Syntheses, (1971), 13:92-94.

Nicholls et al, Some useful derivatives of dodecacarbonyltiosmium, Inorganic Syntheses, (1990), 28:232-233.

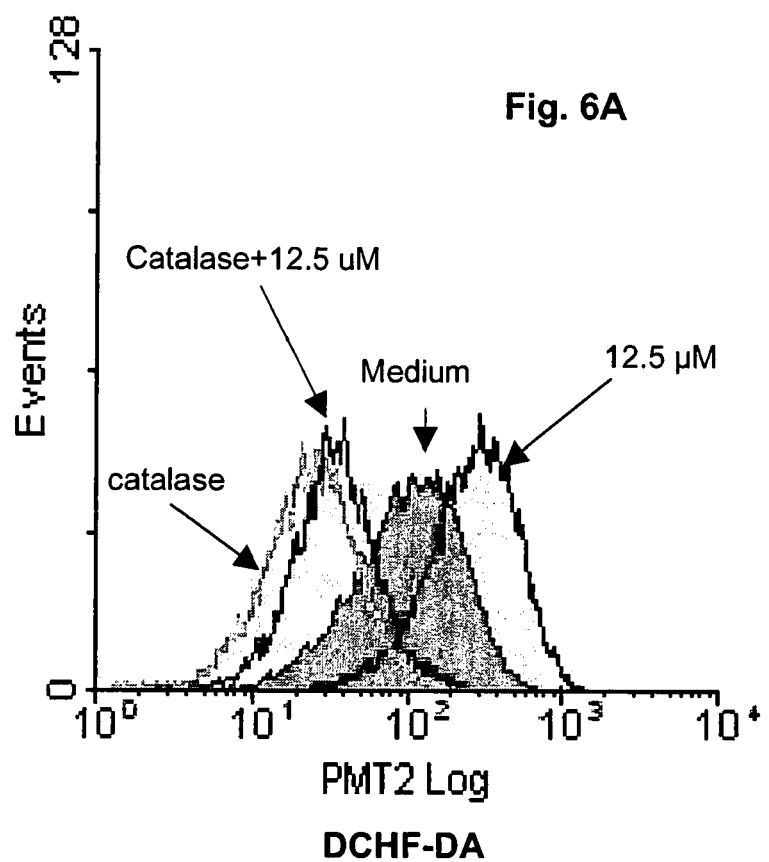
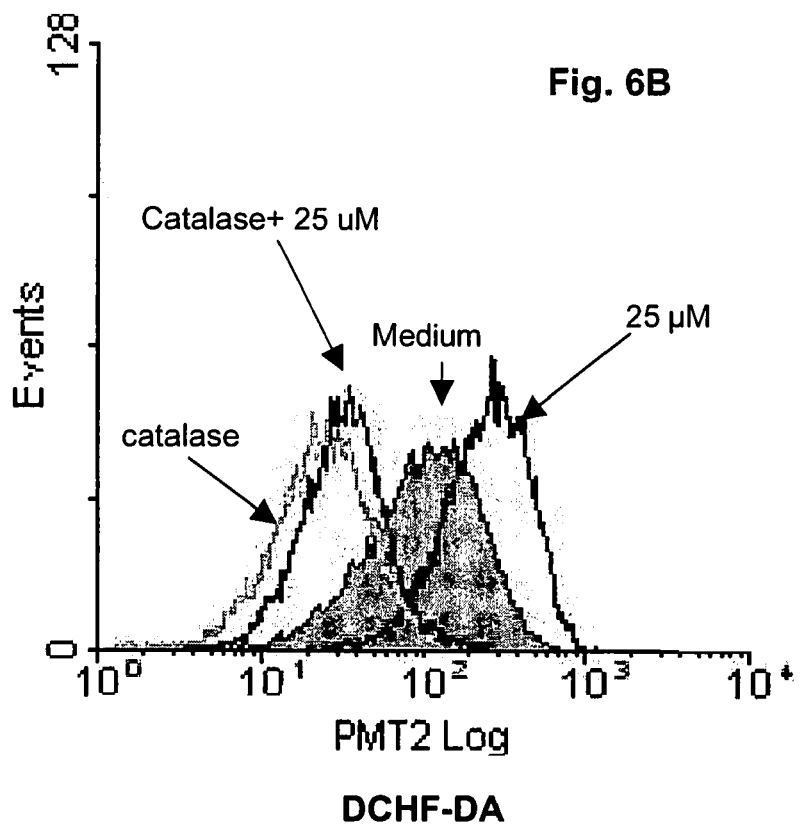

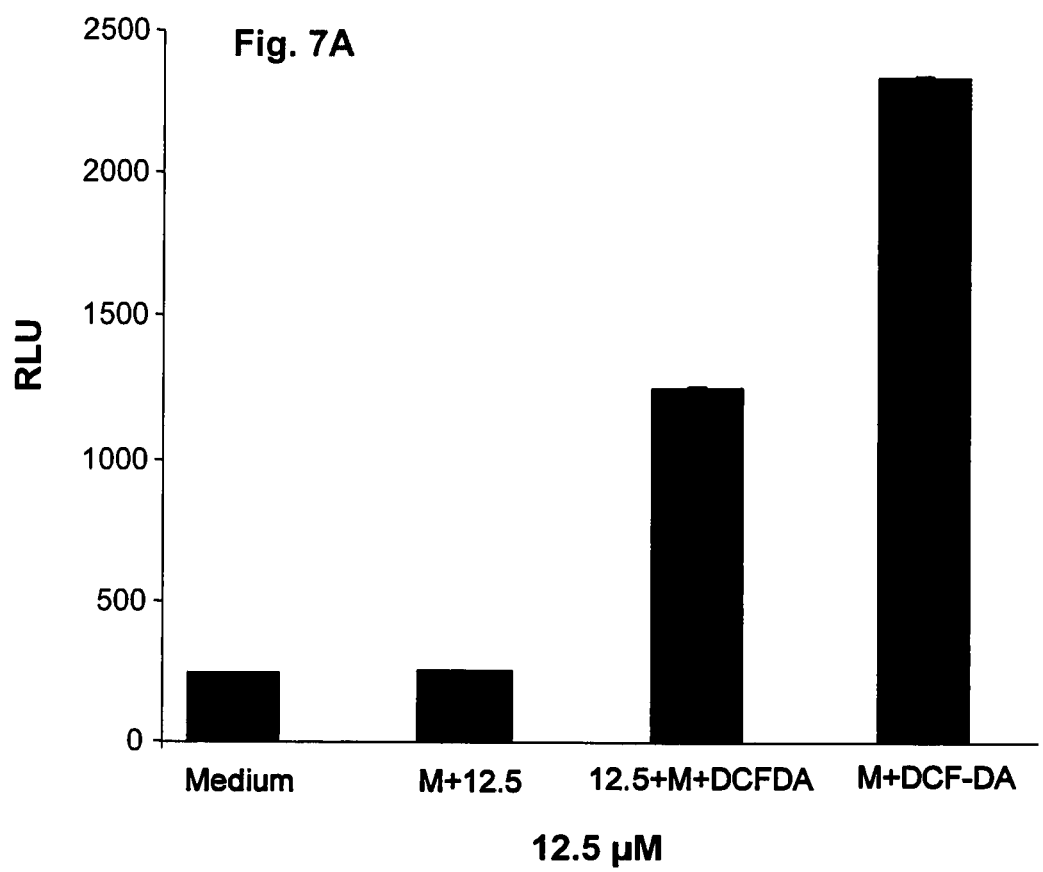
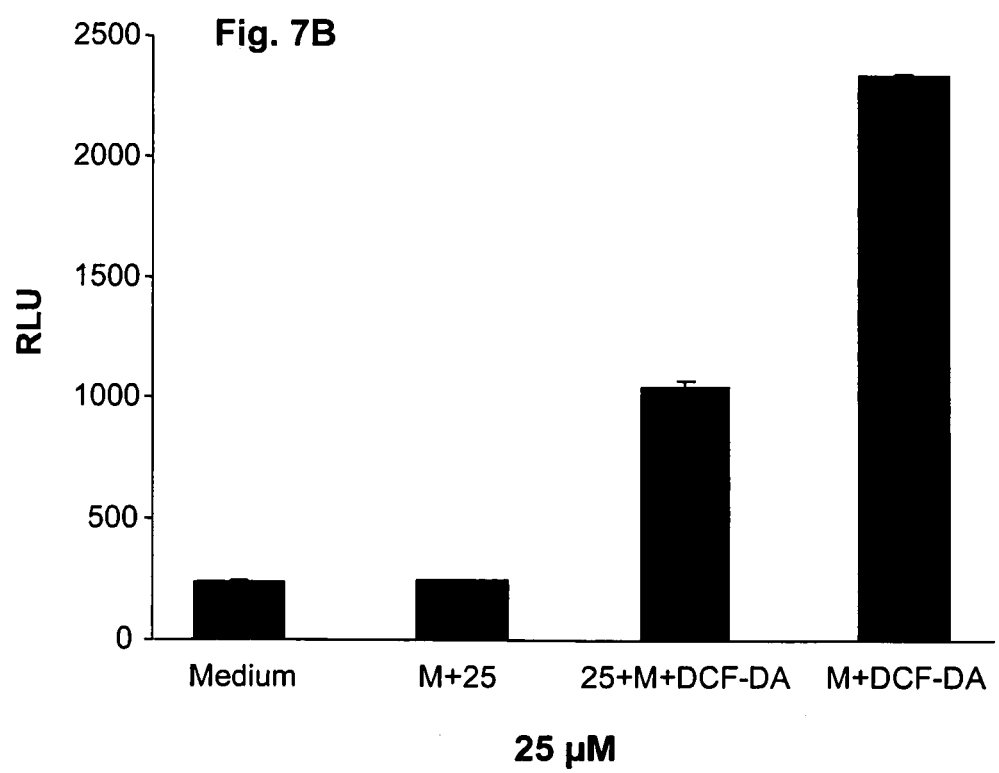

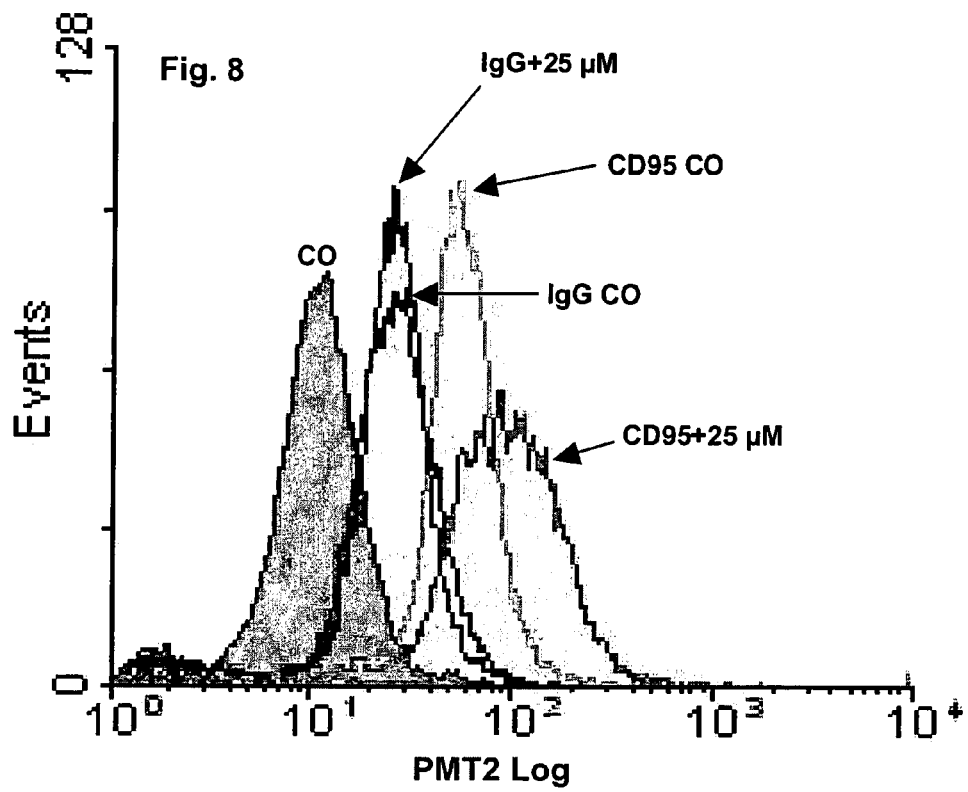
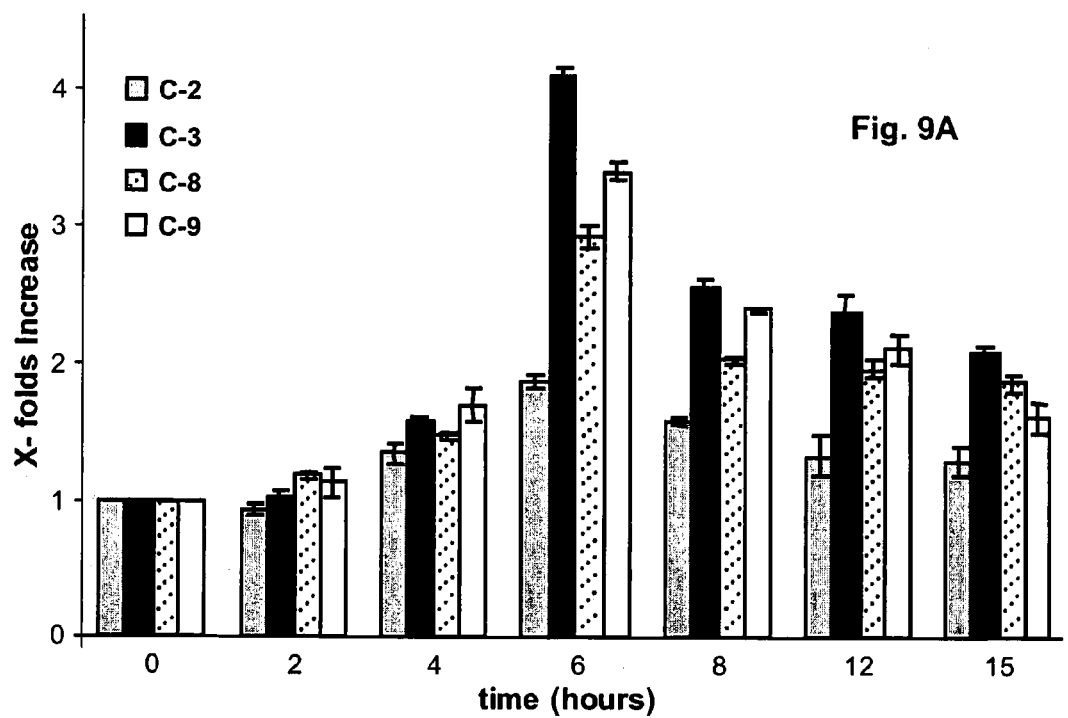

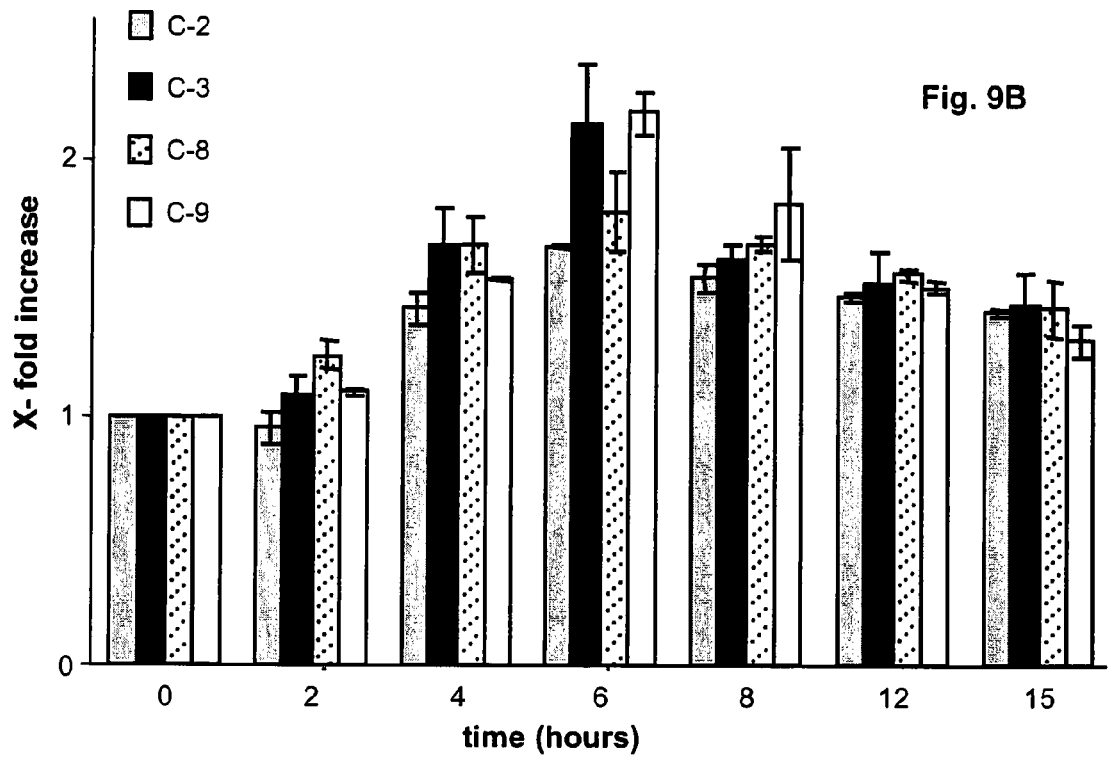
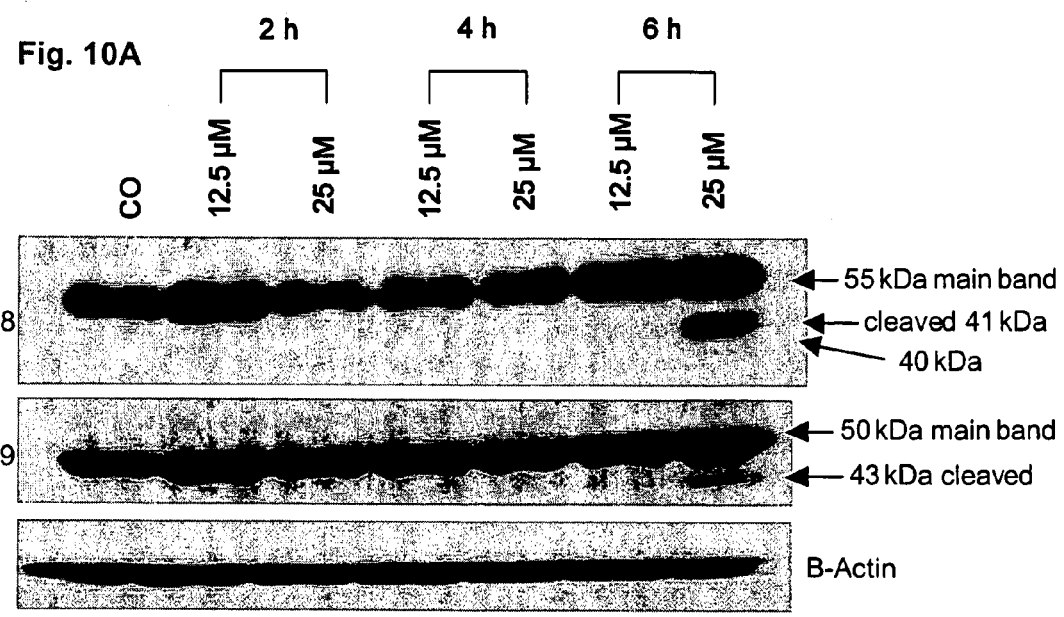

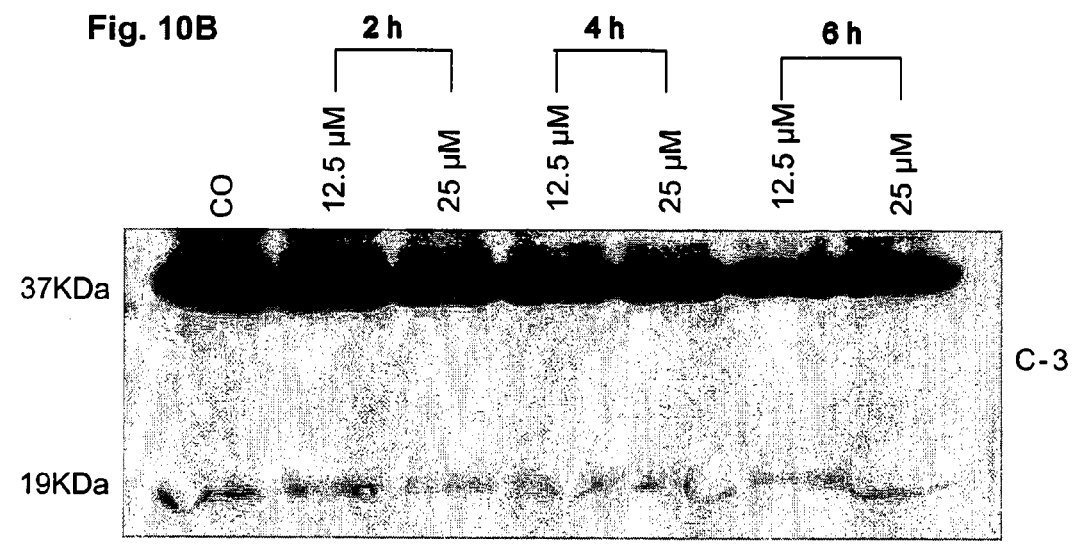
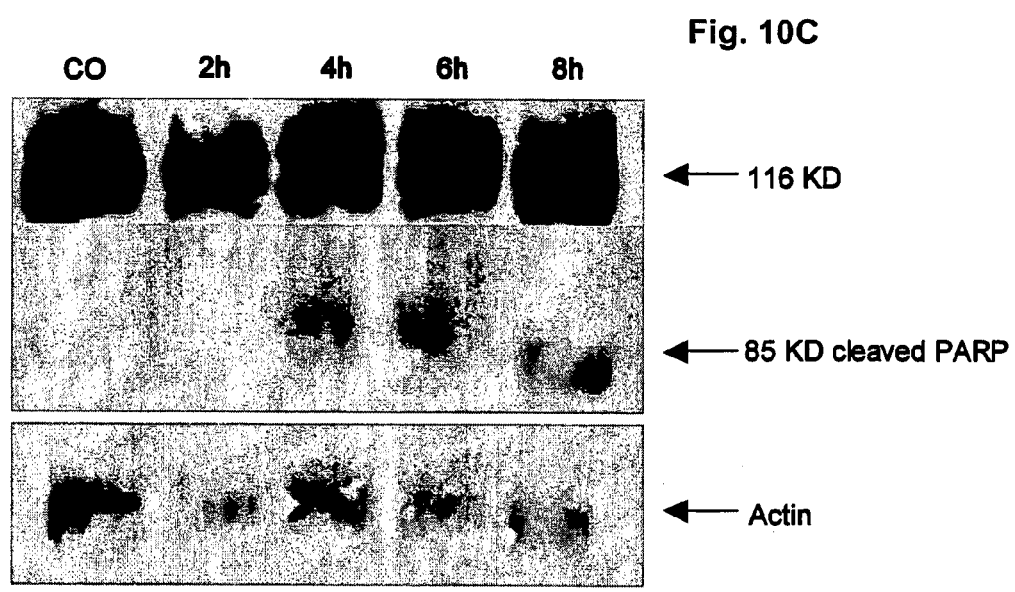

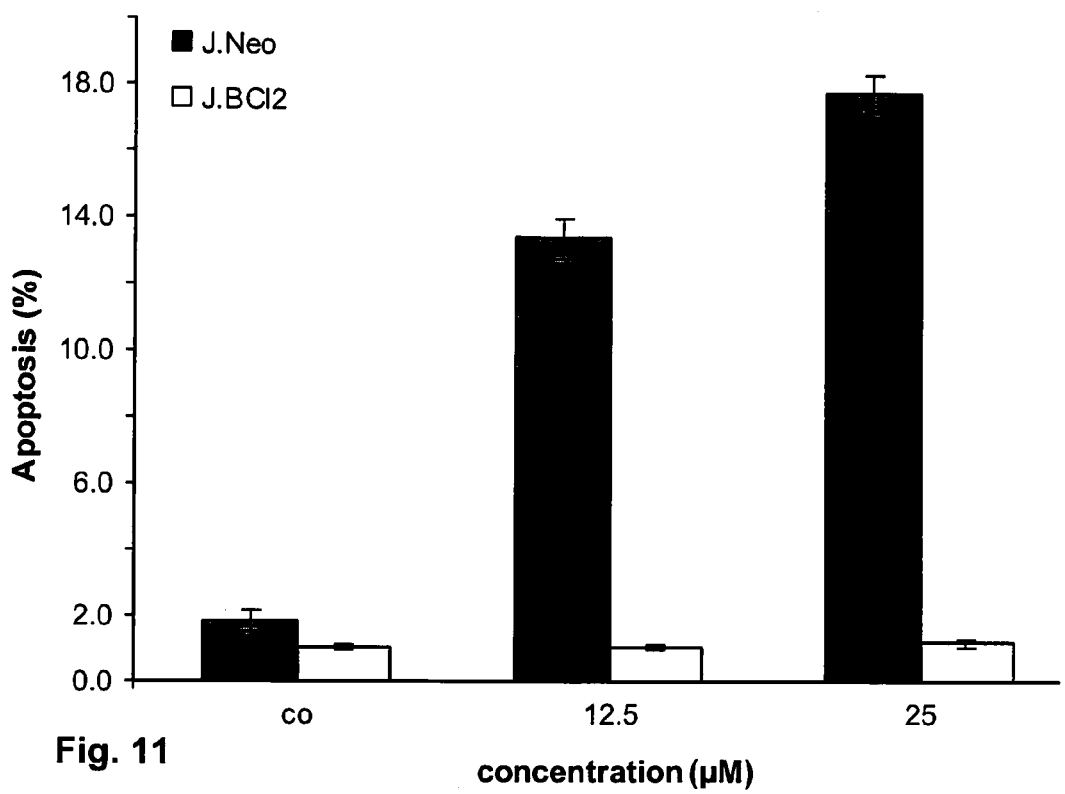
Fig. 11
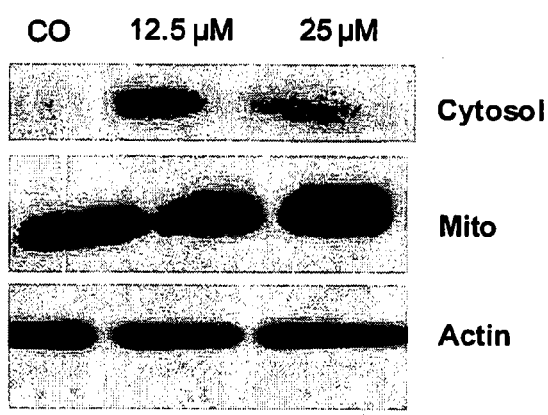
Fig. 12A
Fig. 12B
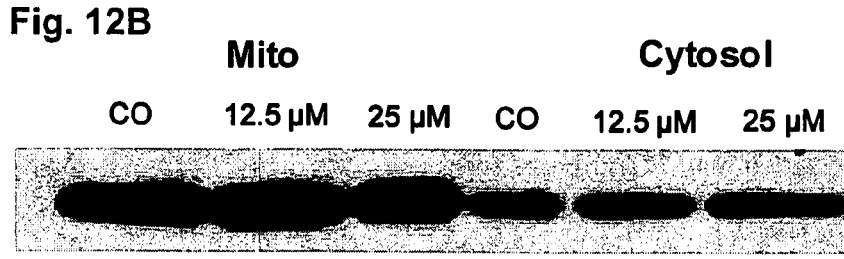

METAL TRIANGULO COMPOUND AND METHODS OF USING THE SAME

FIELD OF THE INVENTION

The present invention relates to a metal triangulo compound and methods of its use. The invention also provides a method of inducing apoptosis in a cell as well as a method of preventing carcinogenesis.

BACKGROUND OF THE INVENTION

Cancer is a major cause of death worldwide, being the second-leading cause of death in developed countries, and even the number one cause of death in e.g. Australia, Japan, Korea, Singapore and the male population of the UK and Spain. The number of people who develop cancer each year is increasing. Nevertheless cancer therapy has not managed to decrease cancer mortality in the last three decades.

The failure of a cell to undergo apoptosis, programmed cell death, is a major factor contributing to occurrence of cancer. Most anti-cancer drugs and gamma-, irradiation exert their lethal effect by inducing apoptosis. Chemotherapy is thus currently largely based on the cytotoxic effect, in some cases also on a true cytostatic effect, of a compound used, for example by way of DNA-alkylation, inhibition of mitosis, interference with metabolism via antimetabolites or structural analogs, and DNA intercalation of antibiotics.

It is an object of the invention to provide a compound suitable for inducing apoptosis in a cell.

It is a further object of the invention to provide a method of inducing apoptosis in a cell.

Another object of the invention is to provide a method of preventing carcinogenesis (cancerogenesis) in a cell.

Another object of the invention is to provide a pharmaceutical composition for treating a tumour/cancer and/or preventing carcinogenesis in a cell.

SUMMARY OF THE INVENTION

In one aspect the invention provides a metal triangulo compound, i.e. a trinuclear cluster of triangular structure, of the general formula (I)

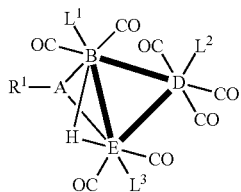

wherein $R^1$ is selected from the group consisting of aliphatic, cycloaliphatic, aromatic, arylaliphatic, and arylcycloaliphatic groups, comprising 0-6 heteroatoms selected from the group consisting of N, O, S, Se and Si, and an electron rich moiety. The electron rich moiety is either (i) a heteroatom selected from the group consisting of N, O, S and Se, or (ii) a functional group selected from —$NH_2$, —COOH, —$CONH_2$, —SH, —Se, —CN, —OH, N=N, N=O, —NS, —NSe, $NC(R^2)$, CN—$R^2$, P—$(R^2)_3$ and —$CF_3$. A is selected from S, Se, N, O, $PO_4$, $PO_3(R^2)$, P—$(R^2)_3$, wherein $R^2$ is H or an aliphatic, cycloaliphatic, aromatic, arylaliphatic or arylcycloaliphatic group, that includes 0-6 heteroatoms selected from the group N, O, S, Se and Si. $L^1$, $L^2$ and $L^3$ are ligands independently selected from CO, —$NC(R^2)$, CN—$R^2$ and —P—$(R^2)_3$, CO, $NCCH_3$ and P—$R^2$, wherein $R^2$ is H or an aliphatic, cycloaliphatic, aromatic, arylaliphatic or arylcycloaliphatic group, that includes 0-6 heteroatoms selected from the group N, O, S, Se and Si. B, D and E are an independently selected metal atom of the group osmium, ruthenium, rhenium, iridium, tin and rhodium.

In a further aspect the inventions provides a method of forming a metal triangulo compound of the general formula (I). The method includes providing a compound of general formula $R^1$-AH. $R^1$ is an aliphatic, cycloaliphatic, aromatic, arylaliphatic or arylcycloaliphatic group, which includes 0-6 heteroatoms selected from the group N, O, S, Se and Si. $R^1$ further includes an electron rich moiety. The electron rich moiety is either (i) a heteroatom selected from the group consisting of N, O, S and Se, or (ii) a functional group selected from the group consisting of —$NH_2$, —COOH, —$CONH_2$, —SH, —Se, —CN, —OH, N=N, N=O, —NS, —NSe, $NC(R^2)$, CN—$R^2$, P—$(R^2)_3$ and —$CF_3$. A is selected from the group consisting of S, Se, O, N, $PO_4$, $PO_3(R^2)$, P—$(R^2)_3$, wherein $R^2$ is H or selected from the group consisting of H, aliphatic, cycloaliphatic, aromatic, arylaliphatic, and arylcycloaliphatic groups, comprising 0-6 heteroatoms selected from the group N, O, S, Se and Si. The method further includes contacting the compound of general formula $R^1$-AH with a compound of formula (III)

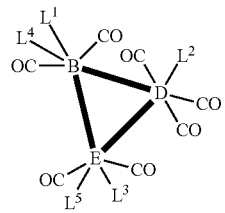

In this formula B, D and E are an independently selected metal atom of the group osmium, ruthenium, rhenium, iridium, tin and rhodium. $L^1$, $L^2$ and $L^3$ are ligands independently selected from CO, —$NC(R^2)$, CN—$R^2$ and —P—$(R^2)_3$, with $R^2$ as defined above. $L^4$ and $L^5$ are independently from one another NC—$CH_3$, CO, NO or H.

In another aspect the inventions provides the use of a metal triangulo compound of general formula (I) in the manufacture of a medicament for inducing apoptosis in a cell or for preventing carcinogenesis in a cell.

In a related aspect the inventions provides a method of inducing apoptosis in a cell. The method includes administering a metal triangulo compound of general formula (I).

In a further the inventions provides a method of preventing carcinogenesis in a cell. The method includes administering a metal triangulo compound of general formula (I).

In yet another aspect the invention provides a pharmaceutical composition for inducing apoptosis in a cell and/or preventing carcinogenesis in a cell. The pharmaceutical composition includes a metal triangulo compound of general formula (I) or a pharmaceutically acceptable salt thereof. The pharmaceutical composition also includes a carrier or diluent.

DETAILED DESCRIPTION OF THE INVENTION

The present invention provides a metal triangular compound of the general formula (I):

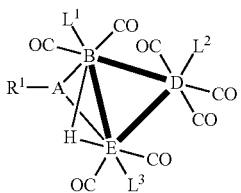

In this formula $R^1$ may be an aliphatic, cycloaliphatic, aromatic, arylaliphatic, or arylcycloaliphatic group that includes 0-6 heteroatoms (i.e. atoms that differ from carbon) and typically has a main chain of a length of 1 to about 20 carbon atoms. Respective heteroatoms may for instance be N, O, S, Se or Si. The aliphatic, cycloaliphatic, aromatic, arylaliphatic, or arylcycloaliphatic moiety may also include other polar, non-polar, saturated or unsaturated groups, including for example an epoxy group. In some embodiments $R^1$ is a mono- to hexacyclic aromatic moiety that includes 0 to 4 heteroatoms. $R^1$ furthermore includes an electron rich moiety. The electron rich moiety is either (i) a heteroatom such as N, O, S and Se, or (ii) a functional group. Examples of a respective functional group include, but are not limited to, —$NH_2$, —$NHR^2$, —CO, —COOH, —$CONH_2$, —$CONHR^2$, —SH, —$SO_4H$, —$SO_4R^2$, —$SO_2R^2$, —Se, —CN, —SCN, —NC, —NS, —NSe, —OH, —N=N, —N=O, —$ONHR^2$, $NC(R^2)$, CN—$R^2$, P—$(R^2)_3$ and —$CF_3$. To name a few illustrative examples, $R^1$ may in some embodiments be caprylamide-8-yl-, 3-aminocyclohexane-1-yl-, tetrahydrofuran-3-yl- or n-pentanol-5-yl-. In some embodiments $R^1$ may be a heterocyclic bidentate, tridentate or quadridentate moiety. Denticity (symbol κ) refers to the number of bonds via which a moiety can, at least in theory, interact with a metal. Typically it refers to the number non-contiguous donor sites by which a moiety can attach to a metal.

In formula (I) A may be S, Se, O, N, $PO_4$, $PO_3(R^2)$, and P—$(R^2)_3$. The moiety $R^2$ may be H or an aliphatic, cycloaliphatic, aromatic, arylaliphatic or arylcycloaliphatic group that includes 0-6 heteroatoms, typically with a main chain of a length of 1 to about 10, about 15 or about 20 carbon atoms. Respective heteroatoms may for instance be N, O, S, Se and Si. $L^1$, $L^2$ and $L^3$ are independently selected ligands, which may be CO, $NCCH_3$ and P—$R^2$. Again, $R^2$ may be an aliphatic, cycloaliphatic, aromatic, arylaliphatic or arylcycloaliphatic group that includes 0-6 heteroatoms (see above) or H. In some embodiments $L^1$, $L^2$ and $L^3$ are CO. B, D and E are independently selected metal atoms of the group osmium, ruthenium, rhenium, iridium, tin and rhodium. Accordingly, a compound of formula (I) may comprise as centres B, D and E only one kind of metal atom, for example osmium or ruthenium but also two or three different kind of metal atoms, i.e. mixed metal atoms, for example osmium and rhenium.

The following compounds are excluded: decacarbonyl[μ-[3-(diethylamino)-2,2-dimethyl-1-propanethiolato]]-μ-hydrotri-triangulo osmium, decacarbonyl-μ-hydro[μ-[11-(mercapto-κS:κS)undecanoato(2-)]]tri-triangulo hydrogen osmate, decacarbonyl-μ-hydro[μ-[2-(mercapto-κS:κS)ethanolato]]tri-triangulo osmium, d ecacarbonyl[μ-[2-[1-[4-(1-hydroxy-1-methyl ethyl)-2-oxo-6-oxabicyclo[3.1.0]hex-1-yl]ethylidene]hydrazine-carbothioamidato-κS:κS]]-μ-hydrotri-triangulo osmium, decacarbonyl[μ-[2-[1-(6,6-dimethyl-3-oxobicyclo[3.1.0]hex-2-yl)ethylidene]hydrazinecarbothioamidato-κS:κS]]-μ-hydrotri-triangulo osmium, decacarbonyl[μ-[(3aR,3bR,4aR,5aS)-3a,3b,4,4a,5,5a-hexa-hydro-5a-hydroxy-3,4,4-trimethyl-1H-cyclopropa[3,4]cyclopenta[1,2-c]pyrazole-1-carbothioamide-κS1: κS1]]-μ-hydrotri-triangulo osmium, decacarbonyl-μ-hydro[μ-[(1R,3E,4S,6S)-4-(mercapto-κS:κS)-4,7,7-trimethylbicyclo[4.1.0]heptan-3-one oximato]]tri-triangulo osmium, decacarbonyl[μ-(1,2-ethanedithiolato-κS:κS)]-μ-hydrotri-triangulo osmium, eicosacarbonyldi-μ-hydro[μ5-[2,4(1H,3H)-pyrimidinedithionato(2-)-κN1:κS2: κS2:κS4: κS4]]hexa-osmium, eicosacarbonyldi-μ-hydro[μ4-[6-(mercapto-κS:κS)-2(1H)-pyridinethionato(2-)-κS2: κS2hexaosmium, eicosacarbonyldi-μ-hydro[μ4-[2,4(1H,3H)-pyrimidinedithionato(2-)-κS2:κS2:κS4:κS4]]hexaosmium, [μ-(2-aminobenzenethiolato-κS:κS)]decacarbonyl-μ-hydrotri-triangulo osmium, decacarbonyl-μ-hydro[μ-(1-hydroxy-2(1H)-pyridinethionato-κS2:κS2)]tri-triangulo osmium, decacarbonyl-μ-hydro[μ-(2(1H)-pyridinethionato-S:S)]tri-triangulo osmium, decacarbonyl-μ-hydro[μ-(3-hydroxy-2(1H)-pyridinethionato-S:S)]tri-triangulo osmium, undecacarbonyl-μ-hydro[μ-(thio-ureato-S:S)]tri-tri-triangulo osmium, decacarbonyl[μ-(4,6-dimethyl-2(1H)-pyrimidinethionato-S:S)]-μ-hydrotri-triangulo osmium, decacarbonyl[μ-(N,N'-diphenylthioureato-S:S)]-μ-hydrotri-triangulo osmium, decacarbonyl-μ-hydro[μ(phenylthioureato-S:S)]tri-triangulo osmium, triacontacarbonyl[μ6-[1,3,5-triazine-2,4,6(1H,3H,5H)-trithionato(3-)-S:S:S':S':S'':S'']]nonaosmium, decacarbonyl [μ-[3-(diethylamino)-2,2-dimethyl-1-propane-thiolato]]-μ-hydrotri-triangulo osmium, decacarbonyl[μ-(β,β-dimethyl-1-azetidine-propanethiolato)]μ-hydrotri-triangulo osmium, decacarbonyl[μ-(1,3-dihydro-1-methyl-2H-imidazole-2-thionato-S:S)]-μ-hydrotri-triangulo osmium, decacarbonyl [μ-(diethyl-carbamodithioato-S:S)]-μ-hydrotri-triangulo osmium, decacarbonyl[μ-[N-(4-fluoro-phenyl)methanethioamidato-S:S]]-μ-hydrotri-triangulo osmium, decacarbonyl-μ-hydro-[μ-(N-phenylmethanethioamidato-S:S)]tri-triangulo osmium, decacarbonyl-μ-hydro[μ-[N-(4-methylphenypmethanethioamidato-S:S]]tri-triangulo osmium, decacarbonyl-μ-hydro[μ-(N-methylmethanethioamidato-S:S)]]tri-triangulo osmium, decacarbonyl-μ-hydroμ-(2-thiazolidinethionato-S2:S2)]tri-triangulo osmium, decacarbonyl-μ-hydro[μ-(2-imidazolidinethionato-S:S)]tri-triangulo osmium, [μ-(2(3H)-benzoxazolethionato-S:S)]decacarbonyl-μ-hydrotri-triangulo osmium, decacarbonyl[μ-(1,3-dihydro-2H-benz-imidazole-2-thionato-S:S)]-μ-hydrotri-triangulo osmium, [μ-(2(3H)-benzothiazolethionato-S2:S2)]decacarbonyl-μ-hydrotri-triangulo osmium, decacarbonyl-μhydro[2-(phosphino-κP:κP)benzenaminato]tri-triangulo osmium, decacarbonyl-μ-hydro[μ-(2-methyl-4-quinolinaminato-κN4:κN4)]tri-triangulo osmium, decacarbonyl-μ-hydro[μ-(6-phenyl-2-pyridinaminato-κN2:κN2)]tri-triangulo osmium, decacarbonyl-μhydro[μ-(2-thiazolaminato-κN2:κN2)]tri-triangulo osmium, decacarbonyl[μ-(4,5-dihydro-2-thiazolaminato-κN2:κN2)]-μ-hydrotri-triangulo osmium, decacarbonyl-μ-hydro[μ-(4-methyl-2-benzothiazolaminato-κN2: κN2)]tri-triangulo osmium, [μ-(benzo[h]quinoline-2-aminato-κN2:κN2)]decacarbonyl-μhydrotri-triangulo osmium, decacarbonyl-μhydro[μ-[4-[(1E)-(4-nitrophenyl)azo]benzenaminato-κN:κN]]tri-triangulo osmium, decacarbonyl-μ-hydro [μ-(1-piperidineethanaminato-κNN1:κNN1)] tri-triangulo osmium, decacarbonyl-μ-hydro[μ-[1,2,3,4-tetrahydro-1-[1-(imino-κN:κN)ethyl]quinolinato]]tri-triangulo osmium, decacarbonyl[μ-(N,N-dimethylmethanimidamidato-N:N')]-μ-hydrotri-triangulo osmium, decacarbonyl[μ-(6-chloro-2-pyridinaminato-N2:N2)]-μ-hydrotri-triangulo osmium, decacarbonyl[μ-(hydrazinecarboxamidato-N:N)]-μ-hydrotri-triangulo osmium, decacarbonyl[μ-(2,2-dimethylhydrazinecarboxamidato-N:N)]-μ-hydrotri-triangulo osmium, decacarbonyl [μ-[1,2-dihydro-4,6-dimethyl-2-(thioxo-κS:κS)-3-pyridinecarbonitrilato]]-µ-hydrotri-triangulo ruthenium, decacarbonyl[µ-(4,6-dimethyl-2(1H)-pyrimidinethionato-S:S)]µ-hydrotri-triangulo ruthenium, [µ-(1,1'-binaphthalene]-2,2'-diaminato-κN:κN)]-decacarbonyl-µ-hydrotri-triangulo ruthenium) and [µ-(4-aminophenolato-N:N)]decacarbonyl-µ-hydrotri-triangulo ruthenium.

In some embodiments for compounds in which B, D and E are osmium and A is sulphur, the following moieties $R^1$ (see above) are excluded: 3-(diethylamino)-2,2-dimethyl-1-propane-yl-, 1-hydroxy-pyridine-2-yl-, 4,6-dimethyl-pyrimidine-2-yl (including the isomer 4,6-dimethyl-2-hydro-pyrimidine-2-enyl), undecanoic acid-11-yl-, ethanol-2-yl-, mercaptoethan-2-yl-, a 2-substituted ethylidene-hydrazinecarbamidyl-(wherein the substituent is an alicyclic moiety that includes an oxygen-containing functional group and up to 1 oxygen heteroatom), pyridine-2-yl (including the isomer 2-hydro-pyridine-2-enyl), 1-hydroxy-pyridine-2-yl (including the isomer 1-hydroxy-2-hydro-pyridine-2-enyl), 3-hydroxy-pyridine-2-yl (including the isomer 3-hydroxy-2-hydro-pyridine-2-enyl), 6-mercapto-pyridine-yl- (including the isomer 6-mercapto-2-hydro-pyridine-2-enyl), 2-aminobenzene-yl-, diaminomethane-2-enyl-, N-phenyl-diaminomethane-2-enyl-, N,N'-diphenyl-diaminomethane-2-enyl-, N,N'-diethylamino-2,2,-dimethyl-propane-3-yl-, imidazolidine-2-enyl-, 1-methyl-imidazole-2-yl- (including the isomer 1-methyl-2-hydro-imidazole-2-enyl), N,N-diethyl-methanethioamide-1-yl-, N-4-methylphenyl-aminomethane-1-yl (including the isomer N-4-methylphenyl-aminomethylenyl-), 1,3-thiazolidine-2-enyl-, benzimidazoline-2-enyl-, and benzothiazoline-2-yl-.

In some embodiments of the compound of general formula (I) B, D and E are identical. B, D and E may for instance be osmium. In such embodiments the metal triangular compound can be depicted by the following formula (II):

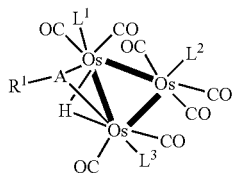

FIG. 3 depicts a few illustrative examples of metal triangular compounds of general formula (I). Further examples include, but are not limited to, [µ-(2(3H)-benzoxazolethionato-S:S)]decacarbonyl-µ-hydrotri-triangulo osmium (CAS-No. 87225-27-2), decacarbonyl-µ-hydro[µ-(2-imidazolidinethionato-S:S)]tri-triangulo osmium (CAS-No. 87225-28-3), decacarbonyl[µ-(1,3-dihydro-2H-benzimidazole-2-thionato-S:S)]-µ-hydrotri-triangulo osmium (CAS-No. 87225-29-4), decacarbonyl-µ-hydro[µ-(3-hydroxy-2(1H)-pyridinethionato-S:S)]tri-triangulo osmium (CAS-No. 178484-90-7), decacarbonyl-µ-hydro[µ-(1-hydroxy-2(1H)-pyridinethionato-κS2:κS2)]tri-triangulo osmium (CAS-No 184695-81-6), decacarbonyl-µ-hydro[µ-(2(1H)-pyridinethionato-κS2:κS2)]tri-triangulo osmium (CAS-No. 178484-91-8), decacarbonyl[µ-(4,6-dimethyl-2(1H)-pyrimidinethionato-S:S)]-µ-hydrotri-triangulo osmium (CAS-No. 162973-40-2), decacarbonyl-µ-hydro[µ-[2-(mercapto-κS: κS)ethanolato]]tri-triangulo osmium (CAS-No. 874748-59-1), decacarbonyl[µ[2-[1-[4-(1-hydroxy-1-methylethyl)-2-oxo-6-oxabicyclo-[3.1.0]hex-1-yl]ethylidene]hydrazinecarbothioamidato-κS:κS]]-µ-hydrotri-triangulo osmium (CAS-No 753453-94-0), eicosacarbonyldi-µ-hydro[µ5-[2,4(1H,3H)-pyrimidinedithionato(2-)-κN1:κS2:κS2:κS4:κS4]]hexa-osmium (6Os—Os) (CAS-No. 252754-16-8), eicosacarbonyldi-µ-hydro[µ4-[6-(mercapto-κS: κS)-2(1H)-pyridinethionato(2-)-κS2:κS2]]-hexa-osmium (6Os—Os) (CAS-No. 252754-15-7), decacarbonyl[µ-[2-[1-(6,6-dimethyl-3-oxobicyclo[3.1.0]hex-2-yl)ethylidene]hydrazinecarbothioamidato-κS:κS]]triangulo osmium (CAS-No. 753453-92-8), decacarbonyl-µ-hydro[µ-[(1R,3E,4S,6S)-4-(mercapto-κS:κS)-4,7,7-trimethylbicyclo[4.1.0]heptan-3-one oximato]]tri-triangulo osmium (CAS-No. 296240-80-7), decacarbonyl[µ-[3aR,3aR,3bR,4aR,5aS)-3a,3b,4,4a,5,5a-hexahydro-5a-hydroxy-3,4,4-trimethyl-1H-cyclopropa[3,4]cyclopenta[1,2-c]pyrazole-1-carbothioamide-κS1:κS1]]-µ-hydrotri-trianguloosmium (CAS-No. 753453-90-6), decacarbonyl[µ-(1,2-ethanedithiolato-κS:κS)]µ-hydrotri-triangulo osmium (CAS-No 288141-54-8), decacarbonyl[µ(diethylcarbamodithioato-S:S)]-µ-hydrotri-triangulo osmium (CAS-No 102931-07-7), decacarbonyl[µ-[N-(4-fluorophenyl)methanethioamidato-S:S]]-µ-hydrotri-triangulo osmium (CAS-No 79737-56-7), decacarbonyl-µ-hydro[µ-(N-phenyl-methanethioamidato-S:S)]tri-triangulo osmium (CAS-No 84027-35-0), decacarbonyl[µ-(β,β-dimethyl-1-azetidinepropanethiolato)]-µ-hydrotri-triangulo osmium (CAS-No 139408-22-3), decacarbonyl-µ-hydro[µ-[N-(4-methylphenyl)methanethioamidato-S:S]]tri-triangulo osmium (CAS-No 84027-36-1), decacarbonyl[µ-(1,3-dihydro-1-methyl-2H-imidazole-2-thionato-κS2:κS2)]-µ-hydrotri-triangulo osmium (CAS-No 103602-16-0), decacarbonyl-µ-hydrobi[µ-(N-methylmethanethioamidato-S:S)]tri-triangulo osmium (CAS-No 84027-37-2), decacarbonyl[µ(N,N'-diphenylthioureato-S:S)]-µ-hydrotri-triangulo osmium (CAS-No 154827-17-5), decacarbonyl-µ-hydro[µ-(phenylthioureato-S:S)]tri-triangulo osmium (CAS-No 154827-16-4), triacontacarbonyl[µ6-[1,3,5-triazine-2,4,6(1H,3H,5H)-trithionato(3-)-S:S:S':S":S"]]nona-osmium (CAS-No 153047-27-9), deca-carbonyl-µ-hydro[µ-(6-phenyl-2-pyridinaminato-κN2:κN2)]tri-triangulo osmium (CAS-No 674316-54-2), decacarbonyl[µ-(4,5-dihydro-2-thiazolaminato-κN2:κN2)]-µ-hydrotri-triangulo osmium (CAS-No 515853-09-5), decacarbonyl-µ-hydro[µ-[4-[(1E)-(4-nitrophenyl)azo]benzenaminato-κN:κN]]tri-triangulo-osmium (CAS-No. 252667-73-5), deca-carbonyl-µ-hydro[µ-(4-methyl-2-benzothiazolaminato-κN2:κN2)]tri-triangulo osmium (CAS-No 515853-06-2), [µ-(2(3H)-benzothiazolethionato-S2:S2)]decacarbonyl-µ-hydro-tri-triangulo osmium (CAS-No 87391-66-0), decacarbonyl-µ-hydro[µ-(2-methyl-4-quinolinaminato-κN4:κN4)]tri-triangulo osmium (CAS-No 884650-70-8), undecacarbonyl-µ-hydro[µ-(thioureato-S:S)]tri-triangulo osmium (CAS-No 174909-69-4), [µ-(benzo[h]quinoline-2-aminato-κN2:κN2)]decacarbonyl-µ-hydrotri-triangulo osmium (CAS-No 477211-78-2), decacarbonyl-µ-hydro[µ-[1,2,3,4-tetrahydro-1-[1-(imino-kN: kN)ethyl]quinolinato]]tri-triangulo osmium (CAS-No 175404-50-9), decacarbonyl[µ-(6-chloro-2-pyridinaminato-N2:N2)]-µ-hydrotri-triangulo osmium (CAS-No 84056-22-4), decacarbonyl[µ-(N,N-dimethylmethanimidamidato-N:N')]µ-hydrotri-triangulo osmium (CAS-No 99350-84-2), decacarbonyl[µ-(hydrazinecarboxamidato-N:N)]-µ-hydrotri-triangulo osmium (CAS-No 82456-07-3), decacarbonyl-µ-hydro[µ-(2-thiazolidinethio-nato-S2:S2)]tri-trianguloosmium (CAS-No. 87225-24-9), decacarbonyl[µ-(1,2-dihydro-4,6-dimethyl-2(thioxo-κS:κS)-3-pyridinecarbonitrilato]]-µ-hydrotri-triangulo ruthenium (CAS-No. 673450-94-7), [µ-(1,1'-binaphthalene]-2,2'-diaminato-κN:κN)]decacarbonyl-µ-hydrotri-triangulo ruthenium (CAS-No. 515134-57-3), [µ(4-aminophenolato-N:N)]decacarbonyl-µ-hydrotri-triangulo ruthenium (CAS-No.

136291-92-4), and decacarbonyl[μ-(4,6-dimethyl-2(1H)-pyrimidinethionato-S:S)]-μ-hydrotri-triangulo ruthenium (CAS-No. 162973-43-5).

In some embodiments $R^1$ is a mono- to hexacyclic aromatic moiety that includes 0 to 6 heteroatoms. Indicating $R^1$ as a respective aromatic moiety ("ar") and indicating the numbering of the metal atoms of the osmium triangulo compound of formula (II), the latter may also be depicted as:

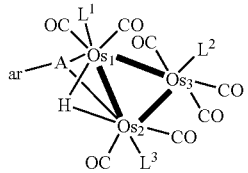

In a compound of formula (I) $L^1$, $L^2$ and $L^3$ may for example CO or a ligand that confers (improved) water solubility such as a phosphine or phosphite ligand having an ionisable group. Illustrative examples of such a phosphine and phosphate ligand L include[P(C$_6$H$_4$SO$_3$Na$_3$)] or [P(OCH$_2$CH$_2$NMe$_3$I$_3$)] as described in Colangelo et al., *Journal of Inorganic Biochemistry* (2005) 99, 505-512. Other ligands L that confer water solubility include PPh$_5$, PPh$_3$, P(Ph)$_2$, bipyridine, 1,3-di-4-pyridylpropane (dpp), 1,2-bis(diphenylphosphino)ethane (dppe), 2,3-bis(2-pyridyl)quinoxaline (dipyridoquinoxaline, dpq), (PPh)$_4$-CH$_2$, [C$_6$H$_4$(PPh$_3$)], TTPInN$_3$, or CH$_3$C(CH$_2$PPh$_2$)$_3$ (Triphos), to name only a few. The ligands $L^1$-$L^3$ may be identical or different, for example, either CO or a water solubility conferring ligand or both may be present.

The term "aliphatic" means, unless otherwise stated, a straight or branched hydrocarbon chain, which may be saturated or mono- or poly-unsaturated and include heteroatoms (see above). An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals normally contain two to twenty carbon atoms and one or two double bonds, such as about two to about ten carbon atoms, and one double bond. Alkynyl radicals normally contain two to twenty carbon atoms and one or two triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, and 3,3 dimethylbutyl. Both the main chain as well as the branches may furthermore contain heteroatoms as for instance N, O, S, Se or Si or carbon atoms may be replaced by these heteroatoms. The term "alicyclic" means, unless otherwise stated, a non-aromatic cyclic hydrocarbon moiety, which may be saturated or mono- or poly-unsaturated. The cyclic hydrocarbon moiety may be substituted with non-aromatic cyclic as well as chain elements. The main chain of the cyclic hydrocarbon moiety may, unless otherwise stated, be of any length and contain any number of non-aromatic cyclic and chain elements. Both the cyclic hydrocarbon moiety and the cyclic and chain substituents may furthermore contain heteroatoms, as for instance N, O, S, Se or Si.

The term "alicyclic" means, unless otherwise stated, a non-aromatic cyclic moiety (e.g. hydrocarbon moiety), which may be saturated or mono- or poly-unsaturated. The cyclic hydrocarbon moiety may also include fused cyclic ring systems and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one ring. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties which that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted.

The term "aromatic" means, unless otherwise stated, a planar cyclic hydrocarbon moiety of conjugated double bonds, which may be a single ring or include multiple fused or covalently linked rings, for example, 2, 3 or 4 fused rings. The term aromatic also includes alkylaryl. Typically, the hydrocarbon (main) chain includes 5, 6, 7 or 8 main chain atoms in one cycle. For illustration purposes, examples of a suitable aromatic moiety include, but are not limited to, benzene, imidazole, benzimidazole, 4H-pyran, pyrazole, pyrazine, pyrrole, pyridazine, furan, indole, benzindole, thiophene, benzofuran, naphthofuran, pyridine, bipyridine, indole, 2H-isoindole, anthrathiobenzene, naphtalene, triazaanthracene, [10]annulen (1,3,5,7,9-cyclodeca-pentaenyl-), [12]annulen, [8]annulen, thia[11]annulen, phenalene (perinaphthene), 1,9-dihydropyrene, chrysene (1,2-benzophenanthrene, anthracene, quinoline, naphthaquinoline, isoquinoline, quinazoline, cinnoline, quinoxaline, oxazol, oxonin, oxepin, benzoxepin, azepin, thiepin, selenepin, thionin, azecin (azacyclodecapentaene), diazecin, thiazine, thiazole, isothiazole, 1H-azepine, dibenzopyridine, azocine, diazocin, benzazocin, 1H-azonine, azaundecin, oxepine, thiepine, thiaphanthrene (naphtho[2,3-b]thiophene), phenanthro[3,2-b]thiophene, 1-oxa-1H-benz[f]indene (naphtho[2,3-b]furan), and furo[3,2-b]pyridine. An example of an alkylaryl moiety is benzyl. The main chain of the cyclic hydrocarbon moiety may, unless otherwise stated, be of any length and contain any number of heteroatoms, as for instance N, O and S.

Accordingly, in some embodiments $R^1$ in formula (I) is an aromatic moiety, such as benzole, imidazole, benzimidazole, 4H-pyran, pyrazole, pyrazine, pyridazine, furan, thiophen, benzofuran, pyridine, bipyridine, indole, 2H-isoindole, naphtalene, anthracene, 9,10-anthracenedione, quinoline, isoquinoline, quinazoline, cinnoline, quinoxaline, thiazine, thiazole, isothiazole, 1H-azepine, dibenzopyridine, azocine, 1H-azonine, oxepine, thiepine, thiaphanthrene (naphtho[2,3-b]thiophene), phenanthro[3,2-b]thiophene, 1-oxa-1H-benz[f]indene (naphtho[2,3-b]furan) and furo-[3,2-b]pyridine.

Accordingly, some embodiments of a metal triangulo compound of general formula (I) may also be called an arylaliphatic compound. By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties include, but are not limited to, 1-ethyl-naphthalene, 1,1'-methylenebis-benzene, 9-isopropylanthracene, 1,2,3-trimethyl-benzene, 4-phenyl-2-buten-1-ol, 7-chloro-3-(1-methylethyl)-quinoline, 3-heptyl-furan, benzomorpholine, 6-[2-(2,5-diethylphenyl)ethyl]-4-ethyl-quinazoline, 1,3-benzodioxole, 9,10-dihydro-anthracene, [3.3]orthocyclophane (5,6,7,12,13,14-hexahydro-dibenzo[a,f]cyclodecene) or 7,8-dibutyl-5,6-diethyl-isoquinoline.

Each of the terms "aliphatic", "alicyclic", "aromatic" and "arylaliphatic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitro-benzenesulfonyl, and methanesulfonyl.

A heteroatom is any atom that differs from carbon. Examples include, but are not limited to N, O, P, S, and Se. Were several heteroatoms are present within the one or more rings of the aromatic moiety, they are independently selected.

In some embodiments where $R^1$ is a mono- to hexacyclic aromatic moiety that includes 0 to 6 heteroatoms (see above) B, D and E, as well as $L^1$, $L^2$ and $L^3$ are identical. $L^1$-$L^3$ may for example be CO, and B, D and E may be osmium, in which case the metal triangulo compound is represented by the following formula (again with the numbering of the metal atoms indicated)

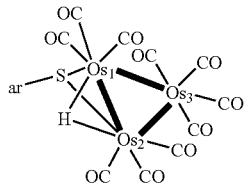

As an illustrative example, in one embodiment a respective osmium triangulo compound is of the structural formula:

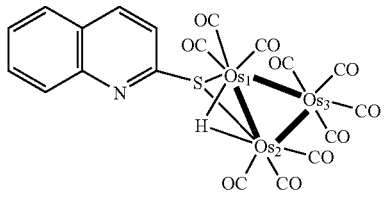

A metal triangular compound of the general formula (I) (see above) may be formed by providing a compound of general formula (III)

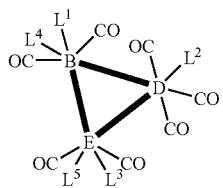

In this formula B, D and E are an independently selected metal atom selected from osmium, ruthenium, rhenium, iridium, tin and rhodium. $L^1$, $L^2$ and $L^3$ are independently selected ligands, which may CO, —NC($R^2$), CN—$R^2$ or —P—($R^2$)$_3$, wherein $R^2$ is H or an aliphatic, cycloaliphatic, aromatic, arylaliphatic, and arylcycloaliphatic group that includes 0-6 heteroatoms selected from the group N, O, S, Se and Si. $L^4$ and $L^5$ are independently selected ligands, which may be of NC—$CH_3$, CO, NO and H.

A reaction of a compound of formula (III) may with a compound of the general formula $R^1$-AH with $R^1$ and A as defined above yields a compound of general formula (I). It has previously been shown that certain ligands such as NC—$CH_3$ are replaced during the formation of a metallic complex with an organic compound (e.g. Hung, J.-T., et al., *Organometallics* (1996) 15, 5605-5612; Smith, R., et al., *Organometallics* (1999) 18, 3519-3527). In this regard the present invention provides a method of forming a metal triangulo compound as defined above. The method includes contacting a compound of general formula (III) with a compound of general formula $R^1$-AH. Examples of $R^1$ include, but are not limited to, quinoline, isoquinoline, imidazole, benzimidazole, pyrazole, pyrazine, indole, benzindole, quinazoline, thiophene, pyridine or naphthaquinoline (see above for further examples), any of which can be substituted. In case, $R^1$ is quinoline, the compound $R^1$-AH may for example be 2-quinolinethiol, 5-quinolinethiol (Chemical Abstracts No. 3056-03-9), 4-quinolinethiol (CAS-No. 51812-96-5), 6-quinolinethiol (CAS-No. 100653-59-6), 8-quinolinethiol (the sodium salt has CAS-No. 2801-16-3), 3-methyl-8-quinolinethiol (CAS-No. 75356-56-8), 4-methyl-2-quinolinethione (CAS-No. 4437-65-4), 6-mercapto-2-quinolinethione (CAS-No. 110131-14-1), 3-methyl-2-quinolinethione (CAS-No. 183206-74-8), 4,7-dimethyl-2-quinolinethione (CAS-No. 64215-48-1), 4-ethyl-2-quinolinethione (CAS-No. 64215-50-5), 8-mercapto-2-quinolinethione (CAS-No. 117536-08-0), 6-phenanthridinethione (CAS-No. 54810-03-6), benzoquinoline-3-thione (CAS-No. 64215-58-3), 3-hydroxy-2-quinolinethione (CAS-No. 34923-72-3), 6-methoxy-2-quinolinethione (CAS-No. 113942-92-0), 5-methyl-1,6-naphthyridine-2-thione (CAS-No. 145316-43-4), 4,6-dimethyl-2-quinolinethione (CAS-No. 41957-23-7), benzisoquinoline-4-thione (CAS-No. 77377-20-9), 4,8-dimethyl-2-quinolinethione (CAS-No. 53761-60-7), 5-sec-pentyl-8-quinolinethiole (CAS-No. 53951-68-1), 5-(2-propenyl)-2-quinolinethione (CAS-No. 876922-09-7), 4-ethyl-7-methyl-2-quinolinethione (CAS-No. 64215-52-7), 7-methyl-4-quinolinethiol (CAS-No. 855766-51-7), 1,2-dihydro-2-thioxo-3-quinolinecarbonitrile (CAS-No. 69513-35-5), 3-quinolinamine (CAS-No. 580-17-6), 4-quinolinamine (CAS-No. 578-68-7), 5-quinolinamine (CAS-No. 611-34-7), 5-sec-octylamino-quinoline (CAS-No. 110378-61-5), 6-quinolinamine (CAS-No. 580-15-4), 7-quinolinamine (CAS-No. 580-19-8), 4-methyl-7-quinolinamine (CAS-No. 114058-79-6), 8-quinolinamine (CAS-No. 578-66-5), 4,7-diaminoquinoline (CAS-No. 40107-15-1), 4-amino-7-methyl-quinoline (CAS-No. 860193-92-6), N-methyl-5-quinolinamine (CAS-No. 7506-67-4), N-methyl-7-quinolinamine (CAS-No. 128278-08-0), 8-sec-octylamino-quinoline (CAS-No. 110336-36-2), 5-isocyano-quinoline (CAS-No. 194281-91-9), 6-methyl-7-quinolinamine (CAS-No. 129844-69-5) and 8-methyl-7-quinolinamine (CAS-No. 116632-62-3). Likewise, if isoquinoline is used as the aromatic moiety, the compound $R^1$-AH may be 1-isoquinolinethiol (CAS-No. 110131-14-1), 5-isoquinolinethiol (CAS-No. 197511-90-3), 4-isoquinolinethiol (CAS-No. 139266-03-8), 7-isoquinolinethiol (CAS-No. 663623-45-8), 8-isoquinolinethiol (CAS- No. 491-33-8), 4-isoquinolinamine (CAS-No. 23687-25-4), 5-isoquinolinamine (CAS-No. 1125-60-6) and 8-isoquinolinamine (CAS-No. 23687-27-6). As a further example, if pyrazole is used as the aromatic moiety, examples of the compound $R^1$-AH include, but are not limited to, pyrazole-4-thiol (CAS-No. 82358-20-1), pyrazole-3-thiol (CAS-No. 82358-00-7), 4-hydroxy-pyrazole (CAS-No. 4843-98-5), 4-aminopyrazole (CAS-No. 28466-26-4), 4-(methyl-amino)-pyrazole (CAS-No. 28466-28-6), 4-amino-1-methyl-pyrazole (CAS-No. 69843-13-6), 4-nitroso-pyrazole (CAS-No. 34690-93-2) and 4-(ethylamino)-pyrazole (CAS-No. 28465-84-1).

The reaction of the compound of formula (III) with the compound $R^1$-AH is typically carried out in an inert organic solvent at elevated temperature. Examples of suitable solvents include hexane, heptane, cyclohexane, benzene, toluene, pyridine, dichloromethane, 1,2-dichloroethane, chloroform, carbon tetrachloride, carbon disulfide, tetrahydrofuran, dioxane, diethyl ether, diisopropylether, ethylene glycol monobutyl ether or tetrahydrofuran.

In some embodiments of a respective method $L^1$ to $L^3$ are CO. The compound of general formula (III) can then also be represented by general formula (IV):

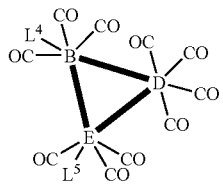

In such embodiments a compound of general formula (V) is formed:

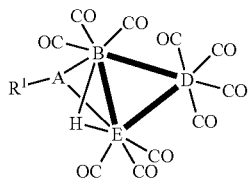

The reaction of a compound of formula (V) with a compound of formula $R^1$-AH results in the formation of a compound of general formula (V):

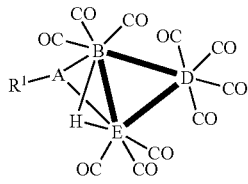

CO ligands in the compound of formula (V) may further be replaced by a reaction with $NC(R^2)$, $CN-R^2$ or $P-(R^2)_3$, wherein $R^2$ is the same as defined above. The obtainable reaction product corresponds to general formula (I), in which at least one of the ligands $L^1$-$L^3$ is $-NC(R^2)$, $CN-R^2$ or $-P-(R^2)_3$. In some embodiments the method of the invention thus includes contacting the compound of general formula (V) with a compound of the group $NC(R^2)$, $CN-R^2$ and $P-(R^2)_3$. In the compound of the general formula $R^1$-AH moieties $R^1$ and A are as defined above.

The present inventors made the surprising finding that compounds of general formula (I) are able to induce apoptosis in a cell, and in particular in a tumour cell. For example, osmium triangulo compounds of different structures have so far only been found to bind to DNA (Rosenberg, E., et al., *J. Organomet. Chem.* (2003) 668, 51-58) and to inhibit telomerase activity (Colangelo, D., et al., *J. Inorg. Biochem.* (2005) 99, 505-512).

Accordingly, the present invention also relates to the use of a metal triangulo compound of formula (I) for inducing apoptosis in a cell, such as a tumour cell, e.g. a cancerous cell or a precancerous cell. A respective use may for example be the manufacture of a medicament for this purpose. Accordingly, the method of the invention includes the use of a compound as defined above, including the use in the manufacture of a medicament. In one aspect the present invention also relates to the use of a compound as defined above for inducing apoptosis in a tumour cell. In this regard the present invention also relates to a compound as defined above for inducing apoptosis in a tumour cell. It is understood that the forgoing and following explanations likewise apply to a respective use and to a compound for the said application(s). In this regard the invention also relates to a metal triangular compound of the general formula (I) as a chemotherapeutic agent.

The respective cell, in which apoptosis is induced, may be obtained from a mammal, such as for example a rat, a cow, a goat, a sheep, a pig, a dog, a mouflon, a guinea pig, a hamster, a chimpanzee, a rhesus monkey and a human. In some embodiments a respective cell is cultured. In other embodiments the cell may be included in a mammal, such as one of the examples above.

In some embodiments the method of the invention includes selectively inducing apoptosis in a cell with a proliferative disorder, such as a tumour cell. Inducing apoptosis in a tumour cell may for example be a therapy for the treatment or prevention of cancer. Inducing apoptosis in a cell such as a tumour cell includes in some embodiments of the present invention cytosolic acidification (see e.g. FIG. 5C). It is noted in this regard that cytosolic acidification is often an early event in apoptosis (e.g. Ahmad, K. A., et al., *Cancer Res.* (2004) 64, 7867-7878).

Inducing apoptosis includes in some embodiments an increase in intracellular reactive oxygen species (ROS). Reactive oxygen species can mediate cytosolic acidification and are one of the most common types of free radicals. They are produced by all aerobic cells during normal cell respiration and metabolism and are generally regulated by antioxidants produced in the body. In every day life, certain factors, such as pollution, and lifestyle factors such as smoking or exercising, increase the production of free radicals. In some embodiments of the method of the present invention the balance between antioxidants production and the generation of reactive oxygen species is disturbed by means of action of a metal triangulo compound as defined above. As a result, programmed cell death, apoptosis is induced. Numerous reports have for instance demonstrated that $H_2O_2$ can induce cell death in cancer cells. Increasing the cellular levels of $H_2O_2$ is thus an efficient way of killing cancer cells. In this regard, experimental evidence also shows that cancer cells are more susceptible to $H_2O_2$-induced cell death than normal cells. Accordingly, the method of the present invention is particularly useful in the killing of cancer cells. As an example, a concentration of 50 µM of $H_2O_2$ has been shown to induced more percentage of cell death in Burkitt's lymphoma cells than 250 µM in normal lymphocytes and normal monocytes (Poh, T. W., and Pervaiz, S., *Cancer Res* (2005) 65, 14, 6264-6274, incorporated herein by reference in its entirety).

Reactive oxygen species are largely produced in mitochondria (for an overview see Adam-Vizi, V., & Chinopoulos, C., *Trends Pharmacol. Sci.* (2006) 27, 12, 639-645), and represent important mediators of cell cycle progression and apoptotic cell death. Examples of reactive oxygen species include, but are not limited to, a peroxyl radical, superoxide ($O_2^-$), ozone, a hydroxyl radical, peroxynitrite, hypochlorous acid and hydrogen peroxide. It is noted that in the method of the present invention intracellular levels of reactive oxygen species are affected. The respective effect of these reactive oxygen species ought therefore not to be confused with extracellular levels of reactive oxygen species, which for instance play an important role in the central nervous system after cerebral ischemia and in certain states of cardiac injury or inflammatory disease.

Apoptotic cells exhibit characteristic hallmarks such as cell size shrinkage, chromatin condensation, DNA fragmentation, plasma membrane blebbing, and the formation of apoptotic bodies. Accordingly, apoptosis of a cell may be monitored visually, where desired. The commitment and execution of apoptosis is dependent upon the activation of a family of cysteine proteases, termed caspases. It can proceed by either an intrinsic or an extrinsic pathway. The main stimulus of the extrinsic pathway involves ligation of death receptors such as a tumour necrosis factor receptor, e.g. a TNF-α receptor and the Apo-1/Fas (CD95) molecule. In some embodiments the method of the present invention involves an increased expression of a tumour necrosis factor (TNF) receptor gene, such as CD95 (see e.g. FIG. 8), TNFR1 (TNF receptor-1) and the TRAIL (TNF-related apoptosis inducing ligand) receptors DR4 and DR5. The intrinsic pathway to apoptosis is mitochondria-dependent and involves an early loss of mitochondrial transmembrane potential ($\Delta\Psi$) and induction of mitochondrial permeability transition (MPT).

In the case of the extrinsic pathway, CD95 ligand (FasL) binds to surface CD95 and initiates the formation of the death-inducing signaling complex (DISC) by recruiting the adaptor molecule Fas-associated death domain containing protein (FADD) and pro-caspase-8 and/or pro-caspase 10 (e.g. Wang, J., et al., *Proc. Natl. Acad. Sci. U.S.A.* (2001) 98, 24, 13884-13888). This results in cleavage-induced activation of caspase 8 and caspase 10, respectively, which initiates the apoptotic program (see e.g. Peter, M. E., et al., *Biochimica et Biophysica Acta* (2005) 1755, 25-36), including the activation of caspase-3, caspase-6 and caspase-7.

Upon the activation of the intrinsic pathway, mitochondria are induced to release a number of proapoptotic factors. This results in caspase-9 activation which in turn can activate caspase-3 (the effector caspase responsible for most of the changes observed in apoptosis) leading to apoptosis. This pathway involves proteins of the Bcl-2 family, which consists of both pro-apoptotic and anti-apoptotic proteins, regulating caspase activation. Pro-apoptotic Bcl-2 family members (e.g. Bak, Bax, Bok/Mtd, Bcl-XS) mediate the release of cytochrome c from the mitochondria, which then participates in initiating the caspase cascade with the activation of caspase 9. While Bax, Bak and Bcl-XS promote apoptosis, other Bcl-2 proteins (e.g. Bcl-2, Bcl-XL, Bcl-W, Bcl-B, Mcl-1, A1/Bfl-1, NR-13) inhibit the apoptotic process. Expression of such antiapoptotic Bcl-2 proteins blocks mitochondrial apoptotic activity, presumably by blocking the release of the factors contained within mitochondria. A third group of proteins of the Bcl-2 family, the BH3-only proteins (e.g. Bid, Bad, Noxa, Bmf, BimL/Bod), induce apoptosis by activating pro-apoptotic proteins such as Bax, or by inhibiting anti-apoptotic proteins such as Bcl-2. The apoptotic death receptor and mitochondrial death pathway converge at caspases-3 activation, which in turn brings about the disassembly of the cell.

However, even in the extrinsic, i.e. death receptor pathway, the involvement of mitochondria has been clearly demonstrated. A second type of signalling from CD95 has been identified in this regard (Type II signal, vs. the above described Type I signal), which requires the intermediacy of caspase-9 and the Bcl-2 family of pro-apoptotic proteins such as Bid and Bax. Similarly to the intrinsic pathway it involves an induction of mitochondrial permeability transition (MPT). This leads to the egress of mitochondrial inter-membranous proteins, such as cytochrome C, to the cytoplasm where it results in the assembly of the apoptosome together with Apaf-1, a homologue of the *C. elegans* cell death protein CED-4, and pro-caspase 9, thus activating caspase-9. Caspase-9 can in turn activate further caspases including caspase-10. Cytochrome c is for instance a required co-factor (together with ATP) for Apaf1 activation, apoptosome formation, and activation of the intrinsic caspase cascade. Activation of caspases then also (cf. Type I signal above) results in a loss of mitochondrial transmembrane potential ($\Delta\Psi$) (Samraj, A. K., et al. *J. Biol. Chem.* (2006) 281, 40, 29652-29659).

Bid, a BH3-only member of the Bcl-2 family capable of inducing apoptosis, is a substrate of caspase-8 and is activated by the extrinsic pathway. Once translocated to mitochondria, the cleaved C-terminal Bid (tBid) potently induces cytochrome c release. Thus, Bid connects the extrinsic, death receptor pathway and the intrinsic, mitochondria pathway and is responsible for cytochrome c release and the downstream caspase activities after Fas/TNF-R1 activation.

In some embodiments the method of the present invention includes an increased release of cytochrome C from mitochondria. Cytochrome c release from mitochondria, which triggers caspase activation, has previously been implicated in apoptosis. In view of the above it is therefore noted that this effect does not indicate an activation, or even the sole activation of the intrinsic pathway. It merely indicates an involvement of mitochondria in the way of action of a metal triangulo compound used in the method of the present invention.

In some embodiments of the method of the present invention increasing expression of a tumour necrosis factor (TNF) receptor gene includes activation of at least one caspase (see e.g. FIG. 9). Examples of respective caspases include, but are not limited to, caspase 2, caspase 3, caspase 8, and caspase 9. Activation of a caspase may include a proteolytic cleavage of an inactive pro-caspase (see FIGS. 9 A and B).

As noted above, the protein Bax is known as a death-promoting member of the Bcl-2 family. Bax has been reported to be able to permeabilise liposomes of lipids of the mitochondrial outer membrane. It has been shown that on the induction of apoptosis, Bax translocates into the outer membrane of mitochondria, where it oligomerises, resulting in mitochondria dysfunction and release of cytochrome c, which subsequently activates caspase pathways. This observation has recently been confirmed to occur upon activation of the Fas-receptor in both cell types known to utilise primarily the extrinsic and cell types known to utilise primarily the intrinsic pathway. It has in a previous publication been shown that both the compound N,N'-dibutyl-thio-4,5-imidazolindion and external $H_2O_2$ induce apoptosis in leukemia cells via a drop in intracellular pH, reactive oxygen species, a drop in mitochondrial transmembrane potential $\Delta\Psi_m$ and a translocation of the protein Bax from the cytosol to mitochondria (Ahmad et al., 2004, supra). The same authors have shown that Bax-deficient cells are resistent to the apoptotic effect of external $H_2O_2$ and show hardly any activation of caspase 9 and 3 in response to external $H_2O_2$.

In contrast to these observations the method of the present invention does generally not require or include a respective sub-cellular translocation of Bax (see FIG. 11B). Without the intent of being bound by theory it is therefore assumed that the absence of a significant change in the status of the BH3 only protein, Bid, argues in favour of a direct effect of a metal triangulo compound of the invention on the mitochondria or via mechanisms that are not clear or not known at present.

In some embodiments the method of the invention, including the use of a metal triangulo compound of the invention, includes inhibiting phosphorylation of the serine/threonine kinase called "protein kinase B" (Akt/PKB). The term "Akt/PKB" as used herein refers to the members of the Aid family, of which currently three members are known (Akt1, Akt2, and Akt3). In many cancers a constitutive activation of Akt/protein kinase B (PKB), a downstream mediator of phosphoinositide 3-kinase (PI3K) activation signal, has been found. PI3K phosphorylates phosphatidylinositol (3,4)-diphosphate to form phosphatidylinositol (3,4,5)-triphosphate (PIP3). PIP3 then recruits Akt/PKB to the membrane where it becomes phosphorylated and thus activated by the phosphatidyl-dependent kinase-1. Akt/PKB can regulate metabolism and maintain cellular energy homeostasis. It has been shown to promote mitochondrial integrity and inhibit cytochrome c release following an apoptotic stimulus in the presence of a phosphorylatable hexose (e.g. glucose or 2-deoxyglucose). The ability of Akt to inhibit apoptosis is thus dependent upon the availability of glucose (for a review see e.g. Robey, R. B. and Hay, N, *Oncogene* (2006) 25, 4683-4696).

Recent evidence strongly suggests that activated Akt/PKB not only contributes to oncogenic proliferative ability but also through phosphorylation of downstream targets, such as Bad, confers resistance to drug-induced apoptosis. Anti-apoptotic signaling by PI3K/Akt occurs at the plasma membrane level, in the cytoplasm and probably at the nucleus. Recent findings point to the likelihood that nuclear PI3K plays an essential role in balancing cell survival and apoptosis also through nuclear phosphatidylinositol (3,4,5) trisphosphate synthesis.

Interestingly, aside from the conventional signals, such as activation of tyrosine receptor kinases, a causal relationship between intracellular reactive oxygen species production, in particular hydrogen peroxide ($H_2O_2$), and activation of Akt/PKB has been described recently; exogenous addition of $H_2O_2$ was shown to activate Akt/PKB phosphorylation. However, other data seem to suggest that activation of the PI3K-Akt pathway could also trigger superoxide ($O_2^-$) production, which would further enhance the downstream effects of this pathway.

Where desired, the progress of apoptosis in a respective cell, e.g. a tumour cell, may be monitored in the method of the invention, for example by propodium iodide staining or flow cytometry analysis, mitochondrial dysfunction (JC-1 staining) or caspase 3 activation. Besides determining apoptosis in a respective cell in some embodiments a method according to the present invention may include determining cell viability in a respective cell. Respective methods are well established in the art.

According to this invention, the method, compound and pharmaceutical composition can be used in the treatment of a cell proliferative disorder, such as a tumour or cancer. Any tumour or cancer may be selected for treatment, including for instance a benign tumour and a metastatic malignant tumour. Examples include, but are not limited to, haematological malignancies and solid tumours. Solid tumours include for instance a sarcoma, arising from connective or supporting tissues, a carcinoma, arising from the body's glandular cells and epithelial cells or a lymphoma, a cancer of lymphatic tissue, such as the lymph nodes, spleen, and thymus. Examples of a solid tumour include, but are not limited to, breast cancer, lung cancer, a brain tumour, a neuroblastoma, colon cancer, rectal cancer, bladder cancer, a liver tumour, a pancreatic tumour, ovarian cancer, prostate cancer and a melanoma.

In some embodiments a method according to the present invention includes contacting a respective cell with a predetermined quantity of a compound of the general formula (I) (see above), such as a tumour cell. In some embodiments at least two different predetermined quantities of a compound of the general formula (I) are used. In some of these embodiments at least a first and a second cell are used. The first cell is contacted with the lower of the two predetermined quantities and the second cell is contacted with the higher of the two predetermined quantities. Respective embodiments may for example be a screening assay, a cytotoxity test or the determination of a dose/response curve.

In some embodiments the first cell (e.g. tumour cell) and the second cell (e.g. tumour cell) are obtained from the same patient. Such a method may for instance be a method of predicting a patient's or an animal's individual response to a metal triangulo compound of the general formula (I). Single nucleotide polymorphisms and individual differences in gene expression usually cause individual differences between patients in responding to a compound that is administered. In some embodiments a respective method of the invention may also be a method of identifying genetic variants that influence a patient's response to a compound of formula (I). Typically the effect of a compound applied to an animal or a patient as a drug is determined by many proteins, so that composite genetic polymorphisms in multiple genes coupled with non-genetic factors determine a response to a compound. A respective method of the invention may thus be a method of determining a patient's genotype, for example to ensure maximum efficacy with minimal adverse effects.

The present invention also relates to a method of preventing carcinogenesis in a cell. The term carcinogenesis (cancerogenesis) as used herein refers to the process by which a normal cell is transformed into cell with a proliferative disorder, in particular into a tumour cell. A respective cell may give rise to a benign tumour and/or a malignant tumour (cancer). A benign tumour does not spread to other parts of the body or invade other tissues. It can nevertheless become a threat to life where it compresses vital structures or is physiologically active (e.g. by producing a hormone). A malignant tumour can invade other organs, spread to distant locations (metastasise) and become life threatening. The respective method includes administering a metal triangulo compound as defined above.

Chemical carcinogens exert their activity through reaction with cellular macromolecules, generally DNA. Formation of carcinogen-DNA adducts can result in mutations that lead to the initiation of tumourigenesis. Among these compounds, polycyclic aromatic hydrocarbons (PAHs) constitute a relevant group because of their widespread environmental prevalence and their relatively high tumourigenic potency (see e.g. Borosky, G. L., J. Org. Chem. (1999) 64, 7738-7744; Mastrangelo, G., et al., *Environmental Health Perspectives* (1996) 104, 11, 1166-1170; Mendelez-Colon, V. J., et al., *Carcinogenesis* (1999) 20, 10, 1885-1891; Rybicki, B. A., et al., *Cancer Letters* (2006) 239, 157-167). Polycyclic aromatic hydrocarbons constitute a large class of compounds formed during incomplete combustion of organic matter and fossil fuels in industrial processes, automobile exhaust, cigarette smoke and charbroiled food. Such compounds are primarily activated by P450 enzymes regulated by the aryl hydrocarbon receptor (Ahr) pathway. The aryl hydrocarbon receptor also plays an important role in the regulation of cell growth and differentiation. Oxidation of polycyclic aromatic hydrocarbons yields hydroxylated polycyclic aromatic compounds as well as polycyclic aromatic compounds that include saturated rings with hydroxy- and epoxy-moieties (e.g. Borosky, 1999, supra; Rybicki et al, 2006, supra). These oxidation products covalently bind to DNA molecules, e.g. at N7- and C8-position of purine bases thereof. The respective adducts may depurinate resulting in apurinic sites in DNA (e.g. Mendelez-Colon et al., 1999, supra). Using immunohistochemical detection of PAH-DNA adducts, a strong correlation between the formation of such adducts and for example carcinogenesis in the prostate has been shown (Rybicki et al, 2006, supra).

It has been shown that PAHs are highly carcinogenic and electron deficient. The formation of covalent DNA adducts is an important first step in the initiation of PAH induced carcinogenesis. Electrophilicity is required for binding to amino active site of DNA. Due to the presence of electron rich site in the metal triangulo compounds of the invention, in some embodiments of the present method of the invention the metal triangulo compound forms a complex with a polycyclic aromatic hydrocarbon. The formation of the respective complex between the metal triangulo compound and the polycyclic aromatic hydrocarbon may then prevent the polycyclic aromatic hydrocarbon from forming a complex with DNA.

The metal triangulo compound according to the present invention may also be used in the form a metabolite or prodrug.

As used herein, the term "prodrug" means a compound which is converted or released within the human or animal body, e.g. enzymatically, mechanically or electromagnetically, into its active form that has medical effects. A "prodrug" is accordingly a pharmacologically inactive derivative of a parent "drug" molecule. It requires spontaneous or enzymatic biotransformation within the physiological system of the human or animal to which it is administered. "Prodrugs" are commonly used in the art to overcome problems associated with stability, toxicity, lack of specificity, or limited bioavailability. They often offer advantages of solubility, tissue compatibility, or delayed release in the mammalian organism. As an illustrative example, a "prodrug" may be a metal triangulo compound with a protective group shielding a moiety or functional group thereof and thereby reversibly suppressing the activity of the metal triangulo compound. A respective "prodrug" may become pharmaceutically active in vivo or in vitro when the protective group undergoes solvolysis or enzymatic removal. As a further illustrative example, a functional group may only be introduced into a metal triangulo compound upon biochemical transformation such as oxidation, phosphorylation, or glycosylation. Thus a respective "prodrug" may only be converted into a compound of general formula (I) by an enzyme, gastric acid, etc. in the human or animal body. The "prodrug" of a compound of general formula (I) may be a hydrate or a non-hydrate. Common "prodrugs" include acid derivatives such as esters prepared by reaction of parent acids with a suitable alcohol (e.g., a lower alkanol), amides prepared by reaction of the parent acid compound with an amine (e.g., as described above), or basic groups reacted to form an acylated base derivative (e.g., a lower alkylamide).

Where applicable, a metal triangulo compound may be used in the form of a free base or any pharmaceutically acceptable salt thereof, e.g. in the case of A including an amino group in the form of the citrate or tartrate. Such forms are known to those of ordinary skill in the art. The metal triangulo compound may also be a hydrate or a non-hydrate.

A metal triangulo compound as defined above, or a pharmaceutically acceptable salt thereof, can be used per se, or in a pharmaceutical composition where it may be mixed with other active ingredients, as in combination therapy, and/or a suitable carrier or diluent. In this regard the present invention also relates to a pharmaceutical composition for inducing apoptosis in a cell and/or preventing carcinogenesis in a cell.

Examples of other active ingredients that may be included in a pharmaceutical composition include, but are not limited to, a nucleic acid alkylator, a nucleoside analogue, an anthracycline, an antibiotic, an aromatase inhibitor, a folate antagonist, an estrogen receptor modulator, an inorganic aresenate, a microtubule inhibitor, a nitrosourea, an osteoclast inhibitor, a platinum containing compound, a retinoid, a topoisomerase 1 inhibitor, a topoisomerase 2 inhibitor, a thymidylate synthase inhibitor, an aromatase inhibitor, a cyclo-oxygenase inhibitor, an isoflavone, a tyrosine kinase inhibitor, a growth factor, a bisphosphonate, and a monoclonal antibody.

Alkylators that may be included in the pharmaceutical composition of the present invention include but are not limited to busulfan (Myleran®, Busilvex®), chlorambucil (Leukeran®), ifosfamide (Mitoxana®, with or without MESNA), cyclophosphamide (Cytoxan®, Neosar®), glufosfamide, melphalan/L-PAM (Alkeran®), dacarbazine (DTIC-Dome®), and temozolamide (Temodar®). As an illustrative example, the compound 2-bis[(2-chloroethyl)amino]tetrahydro-2H-1,3,2-oxazaphosphorine, 2-oxide, also commonly known as cyclophosphamide, is an alkylator used in the treatment of stages III and IV malignant lymphomas, multiple myeloma, leukemia, mycosis fungoides, neuroblastoma, ovarian adenocarcinoma, retinoblastoma, and carcinoma of the breast.

Nucleoside analogues that may be included in the pharmaceutical composition of the present invention include, but are not limited to, cytarabine (Cytosar®) and gemcitabine (Gemzar®), two fluorinated deoxycytidine analogues, fludarabine (Fludara®), a purine analog, 6-mercaptopurine (Puri-Nethol®) and its prodrug azathioprine (Imuran®).

Anthracyclines that may be included in the pharmaceutical composition of the present invention include, but are not limited to, doxorubicin (Adriamycin®, Doxil®, Rubex®), mitoxantrone (Novantrone®), idarubicin (Idamycin®), valrubicin (Valstarg), and epirubicin (Ellence®). As one example the compound (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione, more commonly known as doxorubicin, is a cytotoxic anthracycline antibiotic isolated from cultures of *Streptomyces peucetius* var. *caesius*. Doxorubicin has been used successfully to produce regression in disseminated neoplastic conditions such as acute lymphoblastic leukemia, acute myeloblastic leukemia, Wilm's tumour, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma.

Antibiotics that may be included in the pharmaceutical composition of the present invention include but are not limited to dactinomycin, actinomycin D (Cosmegen®), daunorubicin/daunomycin (Cerubidine®, DanuoXome®), bleomycin (Blenoxane®), epirubicin (Pharmorubicin®) and mitoxantrone (Novantrone®). Aromatase inhibitors useful in the practice of the present invention include but are not limited to anastrozole (Arimidex®) and letroazole (Femara®). Bisphosphonate inhibitors that may be included in the pharmaceutical composition of the present invention include but are not limited to zoledronate (Zometa®).

Cyclooxygenase inhibitors that may be included in the composition of the present invention include but are not limited to acetylsalicylic acid (Aspiring), celecoxib (Celebrex®) and rofecoxib (Vioxx®, Ceoxx®, Ceeoxx®). Estrogen receptor modulators that may be included in the composition of the present invention include but are not limited to tamoxifen (Nolvadex®) and fulvestrant (Faslodex®). Folate antagonists that may be included in the composition of the present invention include but are not limited to methotrexate (Trexall®, Rheumatrex®) and trimetrexate (Neutrexin®). As an illustrative example, the compound (S)-2-(4-(((2,4-diaminopteridin-6-yl)methyl)methylamino)-benzamido)pentanedioic acid, commonly known as methotrexate, is an antifolate drug that has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides.

Inorganic arsenates that may be included in the composition of the present invention include but are not limited to arsenic trioxide (Trisenox®). Microtubule inhibitors (as used herein, a "microtubule inhibitor" is any agent that interferes with the assembly or disassembly of microtubules) that may be included in the composition of the present invention include but are not limited to vincristine (Oncovin®), vinblastine (Velban®), paclitaxel (Taxol®, Paxene®), vinorelbine (Navelbine®), docetaxel (Taxotere®), epothilone B or D or a derivative of either, and discodermolide or its derivatives.

Nitrosoureas that may be included in the composition of the present invention include but are not limited to procarbazine (Matulane®), lomustine (CeeNU®), carmustine (BCNU®, BiCNU®, Gliadel Wafer®), and estramustine (Emcyt®). Nucleoside analogs that may be included in the pharmaceutical composition of the present invention include but are not limited to 6-mercaptopurine (Purinethol®), 5-fluorouracil (Adrucil®), 6-thioguanine (Thioguanine®), hydroxyurea (Hydrea®), cytarabine (Cytosar-U®, Depo-Cyt®), floxuridine (FUDR®), fludarabine (Fludara®), pentostatin (Nipent®), cladribine (Leustatin®, 2-CdA®), gemcitabine (Gemzar®), and capecitabine (Xeloda®). As an illustrative example, the compound 5-fluoro-2,4(1H,3H)-pyrimidine-dione, also commonly known as 5-fluorouracil, is an antimetabolite nucleoside analogue effective in the palliative management of carcinoma of the colon, rectum, breast, stomach, and pancreas in patients who are considered incurable by surgical or other means. Another example of a nucleoside analogue is Gemcitabine. Gemcitabine is 2'-deoxy-2',2'-difluoro-cytidine. It is commercially available as the monohydrochloride salt, and as the beta-isomer. It is also known chemically as 1-(4-amino-2-oxo-1-H-pyrimidin-1-yl)-2-desoxy-2,2-difluororibose.

An illustrative example of an osteoclast inhibitor that may be included in the pharmaceutical composition of the present invention is pamidronate (Aredia®). Platinum compounds that may be included in the pharmaceutical composition of the present invention include, but are not limited to, cisplatin (Platinol®) and carboplatin (Paraplatin®). Retinoids that may be included in the pharmaceutical composition of the present invention include but are not limited to tretinoin, ATRA (Vesanoid®), alitretinoin (Panretin®), and bexarotene (Targretin®). Topoisomerase 1 inhibitors that may be included in the pharmaceutical composition of the present invention include, but are not limited to, topotecan (Hycamtin®) and irinotecan (Camptostar®, Camptothecan-11®). Topoisomerase 2 inhibitors that may be included in the pharmaceutical composition of the present invention include, but are not limited to, etoposide (Etopophos®, Vepesid®) and teniposide (Vumon®).

Examples of a tyrosine kinase inhibitors that may be included in the pharmaceutical composition of the present invention include, but are not limited to, dasatinib (Sprycel®), erlotinib (Tarceva®), gefitinib (Iressa®), imatinib (Gleevec®), lapatinib (Tykerb®), sorafenib (Nexavar®) and vandetanib (Zactima®). Examples of a (recombinant) growth factor that may be included in the pharmaceutical composition of the present invention include, but are not limited to, interleukin-11, interferon-α-2b and interleukin-2. An illustrative example of a thymidylate synthase ininitor that may be included in the pharmaceutical composition of the present invention is Raltitrexed®. Examples of a monoclonal antibody that may be included in the pharmaceutical composition of the present invention include, but are not limited to, rituximab (MabThera®) or cetuximab (Erbitux®).

In this regard the method of the present invention of preventing carcinogenesis may also include the combined administration of a metal triangulo compound as defined above and a further compound as named as an active ingredient of the pharmaceutical composition above. As an example, the sensitivity of tumour cells to chemotherapy therapy by such compounds is in some embodiments enhanced by the administration of a metal triangulo compound, or its salt, of the present invention. Without the intend of being bound by theory it is speculated that increased levels of ROS close to the threshold of cytotoxicity may already be produced through the mitochondrial respiratory chain in tumour cells, and that a metal triangulo compound further increases the level of ROS thereby rendering the respective tumour cell particularly susceptible to anti-cancer compounds.

A pharmaceutical composition comprising the compounds of the present invention may be manufactured in a manner that is itself known, e.g., by means of conventional mixing, dissolving, granulating, dragée-making, levigating, emulsifying, encapsulating, entrapping or lyophilising processes.

A pharmaceutical composition for use in accordance with the present invention may be formulated in conventional manner using one or more physiologically acceptable carriers comprising excipients and auxiliaries that facilitate processing of the active compounds into preparations that can be used pharmaceutically. Proper formulation is dependent upon the selected route of administration.

Exemplary routes of administration of a respective compound, including its salt, or pharmaceutical composition include oral, transdermal, and parenteral delivery. Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. One may also administer the compound or pharmaceutical composition in a local rather than systemic manner, for example, via injection of the compound directly into a solid tumour, such as in a depot or sustained release formulation. Furthermore, a respective compound or pharmaceutical composition may be used in a targeted drug delivery system, for example, in a liposome coated with a tumour-specific antibody. Such liposomes may for example be targeted to and taken up selectively by a tumour.

As an illustrative example, for injection, a compound or pharmaceutical composition according to the present invention may be formulated in aqueous solutions, for example in physiologically compatible buffers such as Hanks's solution, Ringer's solution, or physiological saline buffer. For transmucosal administration, penetrants appropriate to the barrier to be permeated are typically used in the formulation. Such penetrants are generally known in the art.

For oral administration, a respective compound or pharmaceutical composition can be formulated readily by combining the active compound with pharmaceutically acceptable carriers well known in the art. Such carriers enable the compounds of the invention to be formulated as tablets, pills, lozenges, dragées, capsules, liquids, gels, syrups, slurries, suspensions and the like, for oral ingestion by a patient to be treated.

Pharmaceutical preparations for oral use can be obtained by adding a solid excipient, optionally grinding a resulting mixture, and processing the mixture of granules, after adding suitable auxiliaries, if desired, to obtain tablets or dragée cores. Suitable excipients are, in particular, fillers such as sugars, including lactose, glucose, sucrose, mannitol, or sorbitol; starches and derivatives thereof, such as, corn starch, dextrin and wheat starch, rice starch, potato starch, hydroxypropyl starch, wheat starch, gelatine, gum tragacanth, methyl cellulose, hydroxypropylmethyl-cellulose, sodium carboxymethylcellulose, and/or polyvinylpyrrolidone (PVP); cellulose preparations such as, for example, methylcellulose, carboxylmethylcellulose and hydroxypropyl-cellulose; inorganic compounds, such as sodium chloride, boric acid, calcium sulfate, calcium phosphate and precipitated calcium carbonate. If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Suitable fluidizing agents include, but are not limited to, magnesium oxide, synthetic aluminium silicate, metasilicic acid, magnesium aluminium oxide, hydrous silicic acid, anhydrous silicic acid, talc, magnesium stearate, and kaolin. Suitable binding agents include, but are not limited to, polyethylene glycol, polyvinyl pyrrolidine, polyvinyl alcohol, gum arabic, tragacanth, sodium alginate, gelatine, and gluten. Suitable stabilisers include, but are not limited to, proteins, such as albumin, protamine, gelatine and globulin; and amino acids and salts thereof. Suitable thickeners include, but are not limited to, sucrose, glycerine, methylcellulose, and carboxymethylcellulose. Suitable pH adjusting agents include, but are not limited to, hydrochloric acid, sodium hydroxide, phosphates, citrates, and carbonates.

Pharmaceutical compositions that can be used orally include, but are not limited to, push-fit capsules made of gelatine, as well as soft, sealed capsules made of gelatine and a plasticiser, such as glycerol or sorbitol. The push-fit capsules may contain the active compound(s) in admixture with filler such as lactose, binders such as starches, and/or lubricants such as talc or magnesium stearate and, optionally, stabilisers. In soft capsules, the compound(s) may be dissolved or suspended in suitable liquids, such as fatty oils, liquid paraffin, or liquid polyethylene glycols. In addition, stabilisers may be added. All formulations for oral administration should be in dosages suitable for such administration.

For buccal administration, a respective pharmaceutical composition may take the form of tablets or lozenges formulated in conventional manner.

For administration by inhalation, a pharmaceutical composition for use according to the present invention may conveniently be delivered in the form of an aerosol spray presentation from pressurised packs or a nebuliser, with the use of a suitable propellant, e.g., dichlorodifluoromethane, trichlorofluoromethane, dichloro-tetrafluoroethane, carbon dioxide or other suitable gas. In the case of a pressurised aerosol the dosage unit may be determined by providing a valve to deliver a metered amount. Capsules and cartridges of e.g. gelatine for use in an inhaler or insufflator may be formulated containing a powder mix of the compound and a suitable powder base such as lactose or starch.

A respective pharmaceutical composition may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilisers or agents that increase the solubility of the compounds to allow for the preparation of highly concentrated solutions.

In some embodiments an active ingredient, such as a compound as described above, may be in powder form for constitution with a suitable vehicle, e.g., sterile pyrogen-free water, before use.

A respective pharmaceutical composition may also be formulated as a rectal composition such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical composition according to the present invention may be administered by, for example, the oral, topical, dermal, ocular, intravenous, intraarticular, rectal, vaginal, inhalation, intranasal, sublingual or buccal route. Accordingly, the present invention also provides administering to an organism, such as a cell or a mammal, a compound of the general formula (I) (see above), including a composition that includes a respective compound. Any cell may be used in the present method of the invention. As an illustrative example, a tumour cell may be used. Examples of suitable mammals include, but are not limited to, a rat, a cow, a goat, a sheep, a pig, a dog, a mouflon, a guinea pig, a hamster, a chimpanzee, a rhesus monkey and a human.

Exemplary routes of administration of a respective compound or pharmaceutical composition include oral, transdermal, and parenteral delivery (see also above). Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. One may also administer the compound or pharmaceutical composition in a local rather than systemic manner, for example, via injection of the compound directly into a solid tumour, such as in a depot or sustained release formulation. Furthermore, a respective compound or pharmaceutical composition may be used in a targeted drug delivery system, for example, in a liposome coated with a tumour-specific antibody. Such liposomes may for example be targeted to and taken up selectively by a tumour.

The amount of active ingredient that is used can be chosen by the skilled person having regard to the usual factors.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognised that various modifications are possible within the scope of the invention claimed. Additional objects, advantages, and features of this invention will become apparent to those skilled in the art upon examination of the following examples thereof, which are not intended to be limiting. Thus, it should be understood that although the present invention is specifically disclosed by exemplary embodiments and optional features, modification and variation of the inventions embodied therein herein disclosed may be resorted to by those skilled in the art, and that such modifications and variations are considered to be within the scope of this invention.

BRIEF DESCRIPTION OF THE DRAWINGS

FIG. 6 shows a further example of reactive oxygen species (ROS) production HL-60 cells ($1\times10^6$) were treated with 12.5 (A) and 25 µM (B) of $[Os_3(CO)_{10}(\mu\text{-}H)(\mu\text{-}S)C_9H_6N]$ for 4 hrs in the presence or absence of 1000 units/mL catalase. Cells were then loaded with DCFH-DA (5 µM) for 15 minutes and the amount of intracellular $H_2O_2$ generated was indicated by the shift in fluorescence as detected by flow cytometry.

FIG. 7 further illustrates reactive oxygen species (ROS) production in HL-60 cells. 12.5 (A) and 25 µM (B) of $[Os_3(CO)_{10}(\mu\text{-}H)(\mu\text{-}S)C_9H_6N]$ was dissolved in culture medium in the absence of cells with or without DCHF-DA dye and $H_2O_2$ production was measured using a spectrofluorometer.

FIG. 8 depicts the upregulation of Cd95 by $[Os_3(CO)_{10}(\mu\text{-}H)(\mu\text{-}S)C_9H_6N]$ in tumour cells. HL60 cells were treated with 25 mM $[Os_3(CO)_{10}(\mu\text{-}H)(\mu\text{-}S)C_9H_6N]$ for 12 hours and surface expression of CD95 was analysed by flow cytometry as described in Materials and Methods. The shaded histograms show unstained cells. Mouse IgG1k was used as an isotype control. At least 10,000 events were counted, and data shown are representative of at least three separate experiments.

FIG. 9 illustrates that $[Os_3(CO)_{10}(\mu\text{-}H)(\mu\text{-}S)C_9H_6N]$ induces caspase activation. Activities of caspases 8, 2, 9, and 3 were determined in lysates of $[Os_3(CO)_{10}(\mu\text{-}H)(\mu\text{-}S)C_9H_6N]$-treated (A) Jurkat and (B) HL 60 cells and shown as fold increase over untreated cells.

FIG. 10 shows the processing of caspases 8 and 9 (A) and caspase 3 (B) as detected by western blotting using specific antibodies. FIG. 10C shows the cleavage of caspase 3 substrate poly(ADP-ribose)polymerase (PARP) in HL-60 cell lysates as detected by western blotting.

FIG. 11 illustrates that $[Os_3(CO)_{10}(\mu\text{-}H)(\mu\text{-}S)C_9H_6N]$ induces DNA fragmentation. Jurkat Neo and Jurkat BCL2 cells were treated with 12.5 and 25 µM of $[Os_3(CO)_{10}(\mu\text{-}H)(\mu\text{-}S)C_9H_6N]$ for 18 hours, immediately fixed in ethanol and stained with PI for DNA content analysis. Sub-G1 population indicates subdiploid DNA content indicative of apoptotic. The DNA fragmentation induced by $[Os_3(CO)_{10}(\mu\text{-}H)(\mu\text{-}S)C_9H_6N]$ is inhibited in BCl2 overexpressing jurkat cells. Data shown are representative of at least three independent experiments.

FIG. 12 illustrates that $[Os_3(CO)_{10}(\mu\text{-}H)(2\text{-}S)C_9H_6N]$ induces apoptosis through the mitochondrial pathway. HL60 cells ($30\times10^6$) were treated with 12.5 (A) and 25 µM (B) of $[Os_3(CO)_{10}(\mu\text{-}H)(\mu\text{-}S)C_9H_6N]$ treated for 12 hours and cytosolic and mitochondria fractions were subjected to SDS-PAGE electrophoresis, transferred to PVDF membrane, and probe with anti-Cyt.C and anti-Bax antibodies (C). Anti-βactin antibody was used to assess equal loading of samples.

In order that the invention may be readily understood and put into practical effect, particular embodiments will now be described by way of the following non-limiting examples.

EXAMPLES

Preparation of Dodecacarbonyltriosmium

Figure 1:
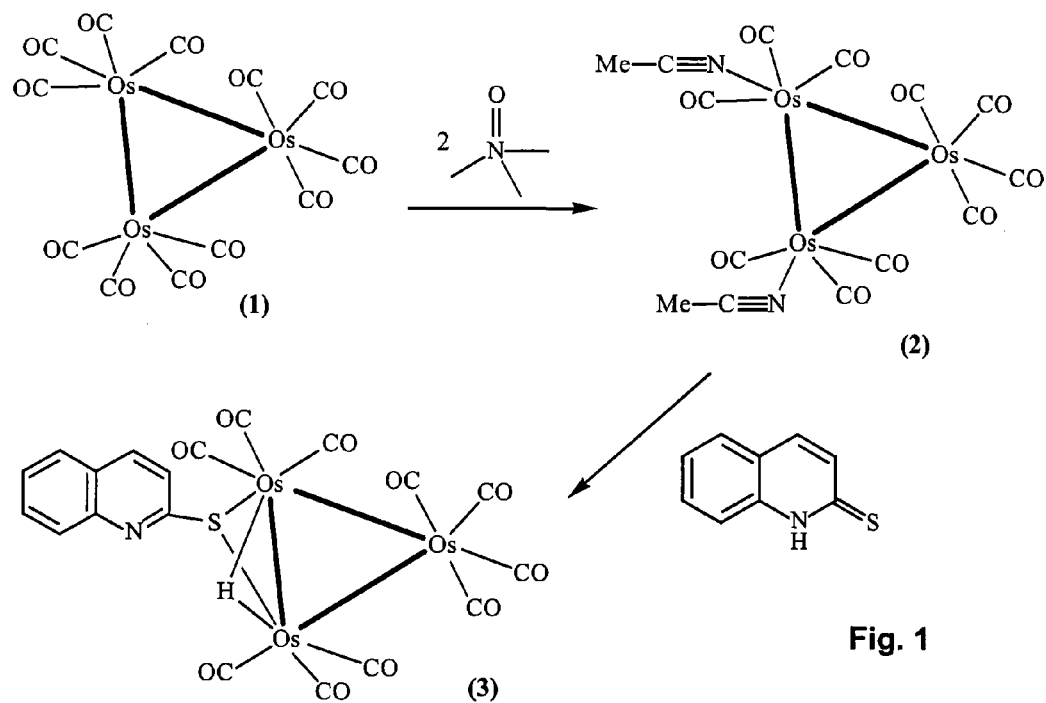
FIG. 1 shows a schematic of a synthesis of $[Os_3(CO)_{10}(\mu\text{-}H)(\mu\text{-}S)C_9H_6N]$ as an illustrative example of a compound of general formula (I).

The present example illustrates the preparation of a precursor of a metal triangular compound as defined above (see compound 1 in FIG. 1). Further information on the synthesis as well as on the synthesis of dodecacarbonylruthenium has previously for instance been provided by Johnson & Lewis (*Inorganic Syntheses* [1971, 13 92-94). Starting materials, osmium tetroxide (OsO$_4$) and 2-quinolinethiol were purchased from Sigma Aldrich.

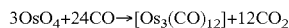

5.0 g (20 mmol) of osmium tetraoxide and 70 ml of anhydrous methanol (freshly distilled from magnesium turnings) were placed in a 250 ml autoclave. Carbon monoxide (CP grade) was filled in to pressure of 40 bars, and then purged to remove the air inside. It was then refilled up to 80 bars and the reaction mixture was heated at 175° C. with vigorously stirring for 10 h. During the heating process, the pressure for the reaction system was about 120 bars. After heating was stopped, the autoclave and its contents were allowed to cool down naturally to room temperature before the remaining carbon monoxide gas was purged (about 12 hours needed). The autoclave was then opened to reveal bright yellow crystals of dodecacarbonyl triosmium suspended in a yellowish-green solution. The products were separated by filtration and washed with ice cold methanol twice and then dried under a slow stream of nitrogen and finally under a vacuum (5.0 g, yield 83%). The obtained product was characterized by IR spectroscopy IR (ν CO) in CH$_2$Cl$_2$: 2068(s), 2034(s), 2013(w), 2000(w) cm$^{-1}$.

Preparation of Bis(Acetonitrile)Decacarbonyltriosmium

The present example illustrates the preparation of a further precursor of a metal triangular compound as defined above (see compound 2 in FIG. 1). Further information on the synthesis has for instance been disclosed by Nicholls & Vargas (*Inorganic Syntheses* (1990), 28 (Reagents Transition Met. Complex Organomet. Synth.), 232-233).

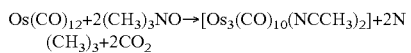

In a 1-L three-necked, round-bottom flask and under an atmosphere of nitrogen, a suspension of [Os$_3$(CO)$_{12}$] (500 mg, 0.55 mmol) was prepared in acetonitrile (300 mL) and dichloromethane (300 mL) (both freshly distilled under nitrogen) which was then heated under reflux for 1 h to dissolve the cluster completely. The solution was allowed to cool to 40° C. Slightly more than two molar equivalents of trimethylamine oxide (100 mg, 1.31 mmol) in acetonitrile (200 mL) were added under nitrogen over a period of 2 h using a pressure-equalized dropping funnel. The mixture was left stirring at this temperature for a further 2 h. After cooling to room temperature, the dark yellow solution was filtered through silica to remove excess trimethylamine oxide; the solvent was then removed under vacuum at room temperature to yield a brown-yellow solid. Yield: 486 mg (95%). The carbonyl region of the infrared spectrum of the product obtained showed the following absorptions (cm$^{-1}$, in dichloromethane) 2079 w, 2025(s,sh), 2020 vs, 1980 m and 1958 w.

Preparation of [Os$_3$(CO)$_{10}$(μH)(μ-S)C$_9$H$_6$N] (MW=1011)

An oven-dried 150 mL two-necked flask was equipped with a magnetic stirrer bar, a rubber septum and a nitrogen inlet. The flask was first flushed with nitrogen, before 30 mL tetrahydrofuran (THF) was added. Bis(acetonitrile)decacarbonyltriosmium, [Os$_3$(CO)$_{10}$(NCMe)$_2$] (150 mg, 0.17 mmol), and 2-quinolinethiol (qtS) (25 mg, 0.17 mmol) were added against the nitrogen flow. The reaction mixture was refluxed at 100° C. and stirred continuously under nitrogen and the colour of the solution turned from yellow to red after a few minutes. The reaction was monitored using TLC until the starting material was completely exhausted at the end of about 4 hours. Excess solvent was removed under vacuum. The residue was dissolved in a minimum amount of dichloromethane and subjected to TLC analysis using a mixed solvent of dichloromethane-hexane (1:3) as eluent. The pure product was placed on mixture of solvents for crystal growing at 4 degree about one month. The final product [Os$_3$(CO)$_{10}$(μ-H)(μ-S)C$_9$H$_6$N], was determined by X-ray crystallography, NMR, Mass and IR. MW=1011

The carbonyl stretching frequencies of the IR spectrum are in the range of 2200 and 1900 cm$^{-1}$, indicating that only terminal carbonyls are found, which agrees with the crystal structure shown in FIG. 1 (as compound (3)). The FAB mass spectrum shows the molecular ion peak at m/z 1011, which is consistent with the formula, [Os$_3$(μ-H)(CO)$_{10}$H$_6$NS]. The $^1$H NMR spectral data for this drug show multiplets in the range of δ 7.8-7.5 ppm for phenyl protons while a triplet at δ 8.0 ppm is assigned to two protons which are deshielded by nitrogen and sulfur atoms. The singlet peak at δ −17.0 ppm shows that there is one bridging hydride, which is further confirmed by single X-ray diffraction studies.

Cells and Culture Conditions

The human promyelocytic leukemia cell line HL60 and Jurkat cells were obtained from ATCC (Rockville, Md.) and maintained in culture in RPMI 1640 supplemented with 10% fetal bovine serum (FBS; GIBCO-BRL, Gaithersburg, Md.) in a humidified incubator at 37° C. and 5% $CO_2$. The cell density in the culture did not exceed $1 \times 10^6$ cells/ml.

Detection of Cytotoxity by a Cell Viability Assay

Figure 2:
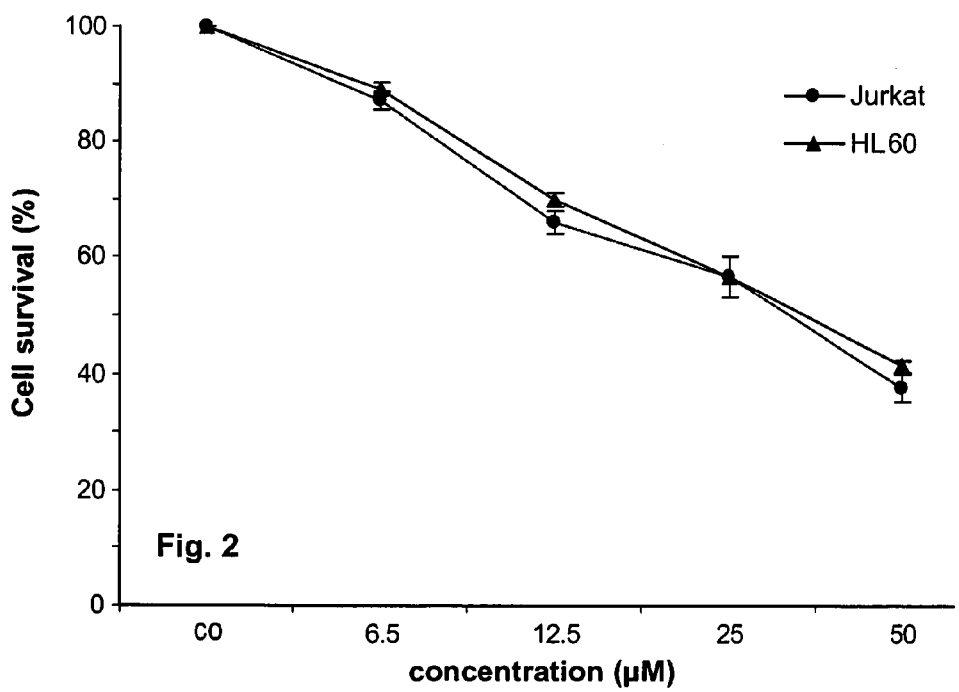
FIG. 2 depicts the detection of cell viability. Anti-tumour activity of $[Os_3(CO)_{10}(\mu\text{-}H)(\mu\text{-}S)C_9H_6N]$ against Jurkat and HL-60 cell lines was determined. A total of $1\times10^6$ cells/ml were exposed to increased concentration of $[Os_3(CO)_{10}(\mu\text{-}H)(\mu\text{-}S)C_9H_6N]$ (0 to 50 µM) for 24 hours and cell death was determined by MTT assay, Data shown are the mean±three independent experiments performed in triplicate.
Figure 3:
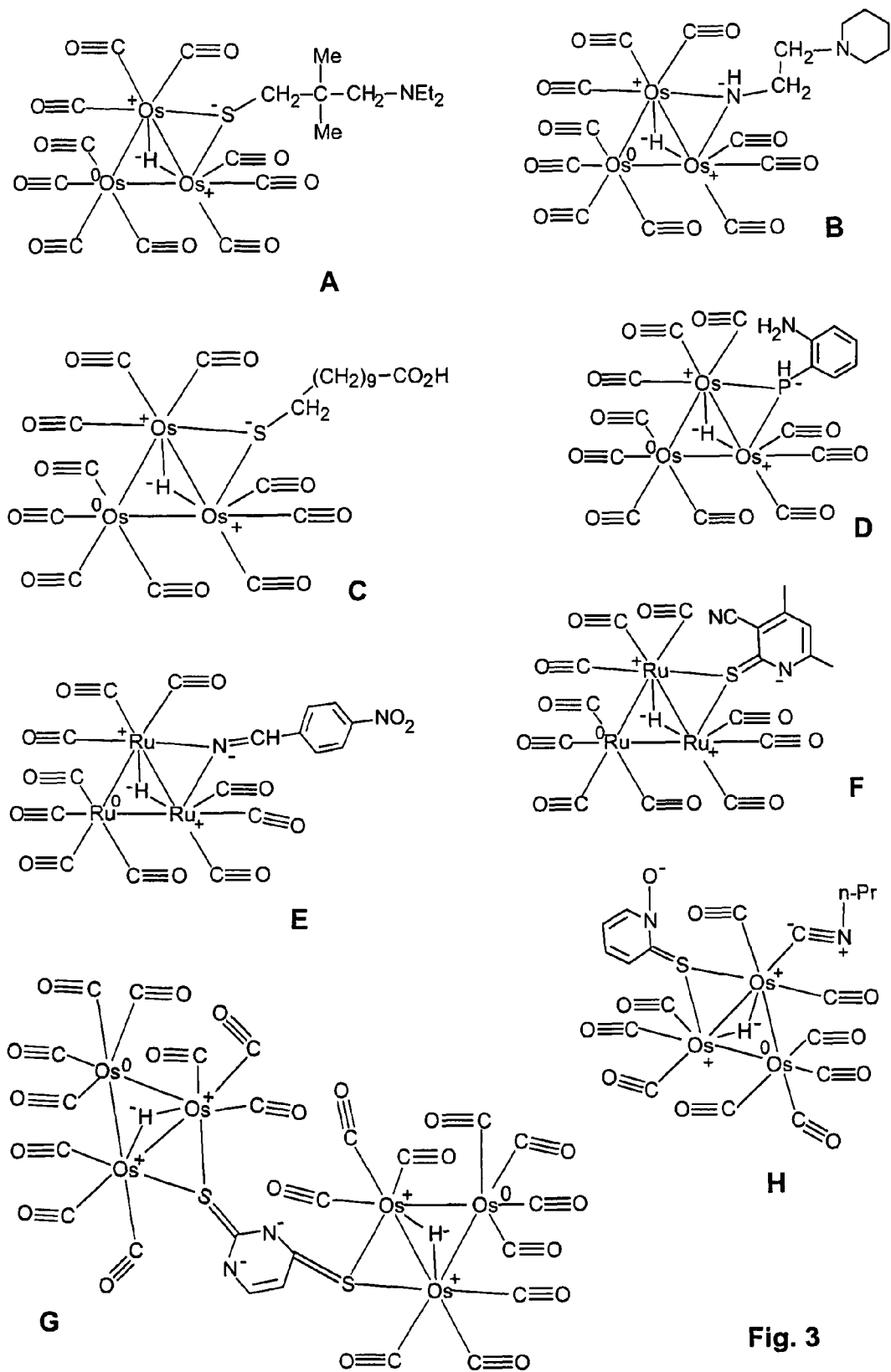
FIG. 3 depicts further examples of compounds of general formula (I): A: decacarbonyl[µ-[3-(diethylamino)-2,2-dimethyl-1-propanethiolato]]-µ-hydrotri-triangulo-osmium (Chemical Abstracts-No. 139408-21-2); B: decacarbonyl-µ-hydro[µ-(1-piperidineethanaminato-κNN1:κNN1)]tri-triangulo-osmium (CAS-No. 219951-95-8); C: decacarbonyl-µ-hydro[µ-[11-(mercapto-κS:κS)undecanoato(2-)]]tri-triangulo-hydrogen osmate (CAS-No. 881200-21-1); D: decacarbonyl-µ-hydro[2-(phosphino-10:0)-benzenaminato] tri-triangulo-osmium (CAS-No. 524745-33-3); E: decacarbonyl-µ-hydro[µ-(4-nitrobenzenemethaniminato-Nα:Nα]] tri-triangulo-ruthenium (CAS-No. 107827-95-2); F: decacarbonyl[m-[1,2-dihydro-4,6-dimethyl-2-(thioxo-κS: κS)-3-pyridinecarbonitrilato]]-µ-hydrotri-triangulo-ruthenium, (CAS-No. 87225-24-9); G: [µ-(2-aminobenzenethiolato-κS:κS)]decacarbonyl-µ-hydrotri-triangulo-osmium (CAS-No. 186509-08-0); H: nonacarbonyl-µ-hydro[µ-(1-hydroxy-2(1H)-pyridinethionato-κS2:κS2)]-[1-(isocyano-κC) propane]tri-triangulo-osmium (CAS-No. 184695-94-1).

HL-60 cell and jurkat cells ($1 \times 10^5$/well) were exposed to increasing concentrations of $[Os_3(CO)_{10}(\mu\text{-H})(\mu\text{-S})C_9H_6N]$ (0 to 50 mM) for 24 hours in a 96 well plate. Cells were supplemented with 3 mg/ml of 3-(4,5-dimethylthiazolyl-2)-2,5-diphenyl tetrazolium bromide (MTT) in plain RPMI 1640 and incubated for 1-2 h at 37° C. The cells were then centrifuged at 3000 rpm for 5 mins before being re-dissolved in 100 μl DMSO+10 μl of Sorensen's glycine buffer (0.1 M glycine, 0.1M NaCl, pH 10.5). Cell viability was determined spectrophotometrically using an automated ELISA reader, with absorbance wavelength of 570 nm. Obtained data are shown in FIG. 2. Data shown are the mean±three independent experiments performed in triplicate. Cell viability is expressed as percentage of cell survival from non-treated control cells with ±SD. The concentration of Os drug inhibiting 50% of cell viability ($IC_{50}$) was around 25 mM (see FIG. 2).

DNA Fragmentation by Propidium Iodide

For cellular DNA content determination, $1 \times 10^6$ cells/ml from each cell line were treated with $[Os_3(CO)_{10}(\mu\text{-H})(\mu\text{-S})C_9H_6N]$. After treatment, cells were washed twice with 1×PBS+1 FBS. Sample preparation and staining with PI for DNA content were performed as described elsewhere (32). Briefly, cell pellets were resuspended in 0.5 ml of 1×PBS+1% FBS and immediately fixed by adding 5 ml of 70% ethanol while vortexing to avoid clumping.

Fixed cells were left at 4° C. for 30 min, centrifuged at 1000×g for 5 min and washed once with 1×PBS+1% FBS. Cell pellets were then suspended in 0.5 ml of PI/RNAse. A solution prepared by adding 1/50 volume of PI stock and 1/40 volume of RNAse. A stock to 1×PBS+1% FBS and incubated for 30 min at 37° C. Stained cells were analyzed by flow cytometry with the excitation set at 488 nm and the emission set at 610 nm (red).

The ability of the cells to scatter light in a forward direction (FS) correlates with cell volume. Os drug-treated cells were analysed for changes in the intensity of FS as compared to untreated control cells. A total of 10,000 cells per sample were studied and data were analyzed by the WINMDI software.

Figure 4B:
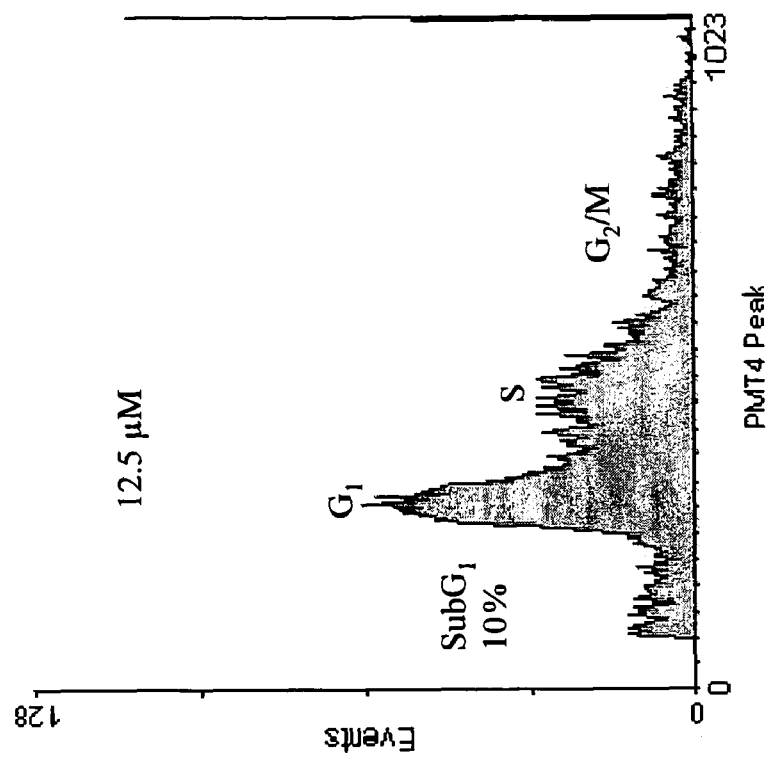
FIG. 4 depicts the detection of DNA Fragmentation. DNA cleavage in $[Os_3(CO)_{10}(\mu\text{-}H)(\mu\text{-}S)C_9H_6N]$-treated tumour cells was assessed using flow cytometric analysis. HL-60 cells were treated with 12.5 and 25 µM $[Os_3(CO)_{10}(pt\text{-}H)(\mu\text{-}S)C_9H_6N]$ for 24 hours, immediately fixed in ethanol, and stained with PI for DNA content analysis. SubG1 population indicates subdiplod DNA content indicative of apoptotic DNA fragmentation. Data shown are representative of at least three independent experiments.
Figure 4A:
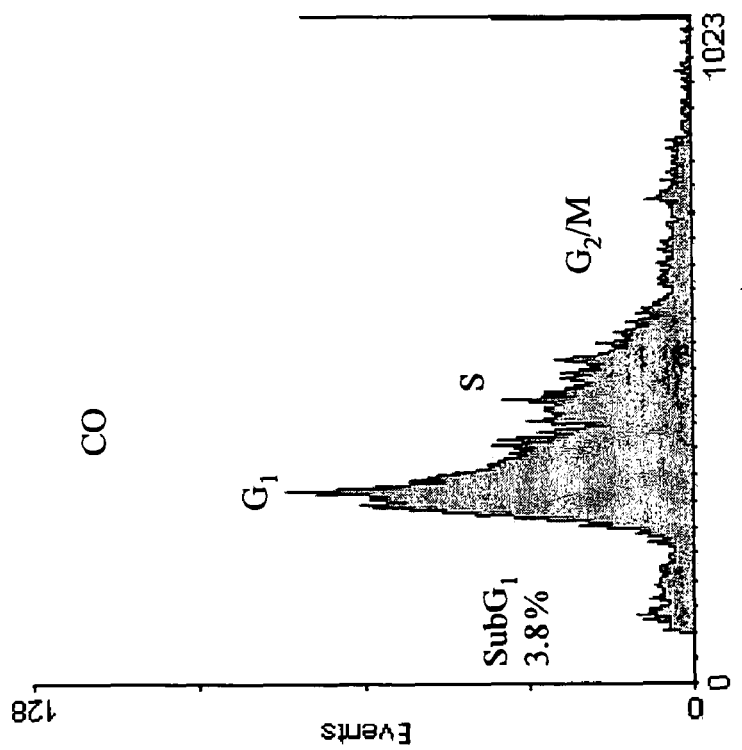
Figure 4C:
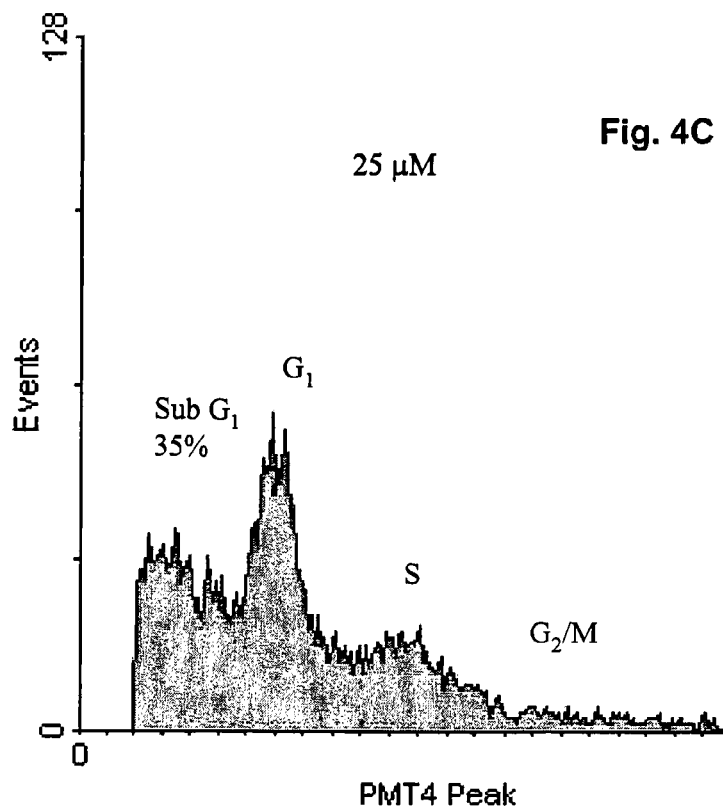

Data are depicted in FIG. 4. Analysis of DNA fragmentation clearly indicated that cell death induced by the osmium triangulo compound was apoptotic in nature (appearance of sub-$G_1$ fraction) as the percentage of sub-diploid DNA increased significantly.

Intracellular Superoxide ($O^{2-}$) Measurement

A lucigenin-based chemiluminescence assay is routinely used in the laboratory as detailed in Clement and Pervaiz (Pervaiz S, Clement M V, Methods Enzymol. (2002) 352, 150-159). In brief, chemiluminescence was monitored using a Berthold Sirius Luminometer (Berthold Detection Systems GmbH, Bleichstralβe/Pforzheim, Germany). Data are described as relative light units/mg of protein (RLU/mg protein). Protein concentration was determined using the Coomassie Plus protein assay reagent from Pierce (Pierce Chemical Company, Rockford, Ill., USA) as detailed by the manufacturer.

Measurement of Intracellular pH with 2',7'-Bis(2-carboxyethyl)-5,6-carboxyfluorescein BCECF)

This example illustrates determining whether and to what extent apoptosis induced by an osmium triangulo compound of the present invention is accompanied by an increase in intracellular ROS production. Cells were exposed to $[Os_3(CO)_{10}(\mu\text{-H})(\mu\text{-S})C_9H_6N]$ for 2 h and 4 h and intracellular $O_2^-$ production was measured by a lucigenin-based chemiluminescence assay.

Intracellular ($pH_i$) was measured by loading cells with membrane-impermeant dye BCECF (Sigma). Briefly, cells ($1 \times 10^6$) before or after exposure (2-12 h at 37° C.) to $[Os_3(CO)_{10}(\mu\text{-H})(\mu\text{-S})C_9H_6N]$ was washed once with HBSS, resuspended in 0.1 ml of HBSS, and loaded with 10 ml of 1 mM BCECF at 37° C. for 30 min in the dark. Cells were then resuspended in 0.5 ml of HBSS and analyzed using a Coulter Epics Elite ESP (Coulter, Hialeah, Fla.) flow cytometer with the excitation set at 488 nm. A minimum of 10,000 events was analyzed, and the ratio of BCECF fluorescence at 525 and 610 was used to obtain intracellular pH from a pH calibration curve. In order to generate a pH calibration curve, cells were loaded with BCECF as above, washed once with HBSS, and then resuspended in high $K^+$ buffer (135 mM $KH_2PO_4$, 20 mM NaCl, and 110 mM $KH_2PO_4$, and 20 mM NaCl with a range of pH between 6.0 and 8.0). Immediately before flow cytometry, cells were loaded with 20 mM nigericin (1 mM stock in absolute alcohol; Sigma), and fluorescence ratio measurements (525 nm/610 nm) of cells in nigericin-containing buffers of a range of pH were then used to relate histogram channel numbers to ipH. Where indicated, ipH was clamped by incubating cells in medium at the required pH in the presence of 1 μg/ml nigericin.

Figure 5A:
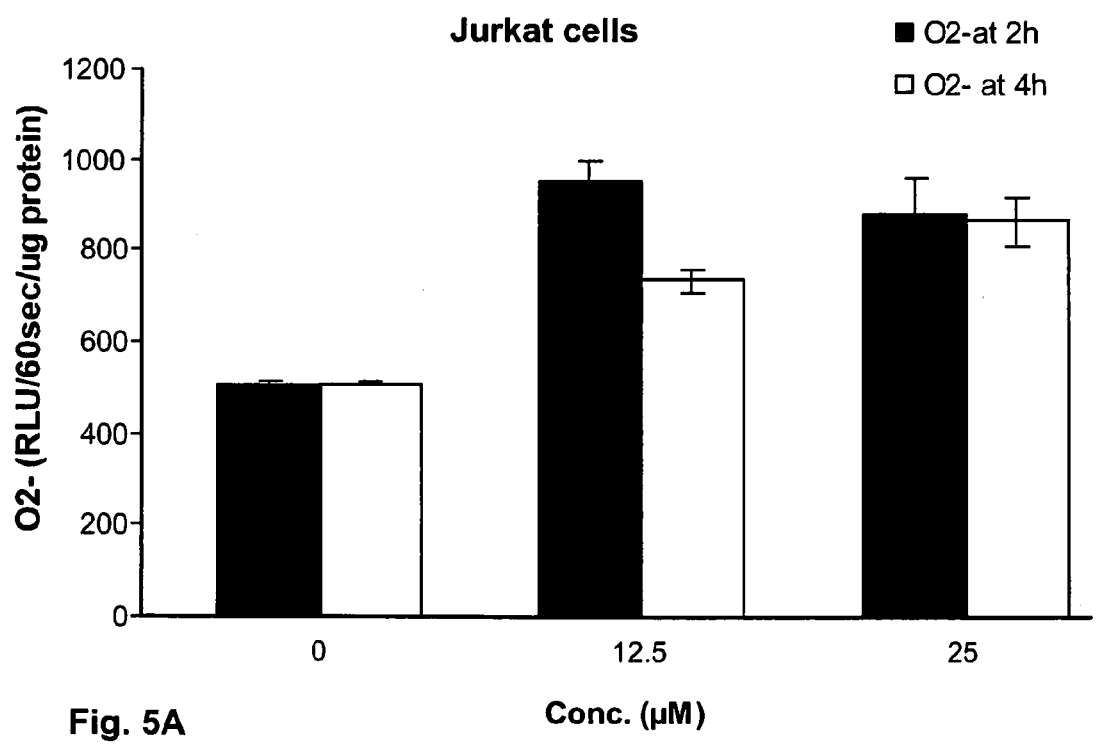
FIG. 5 shows examples of reactive oxygen species (ROS) production and decrease in intracellular $pH_i$. (A) Jurkat cells and (B) HL-60 cells ($2\times10^6$) were incubated with 12.5 and 25 µM $[Os_3(CO)_{10}(\mu\text{-}H)(\mu\text{-}S)C_9H_6N]$ and intercellular $O_2^-$ was measured by a lucigenine-based chemiluminescence assay (C) A, cytosolic pH was determined with the pH-sensitive probe 2',7'-bis(2-carboxyethyl)-5,6-carboxy-fluorescein.
Figure 5B:
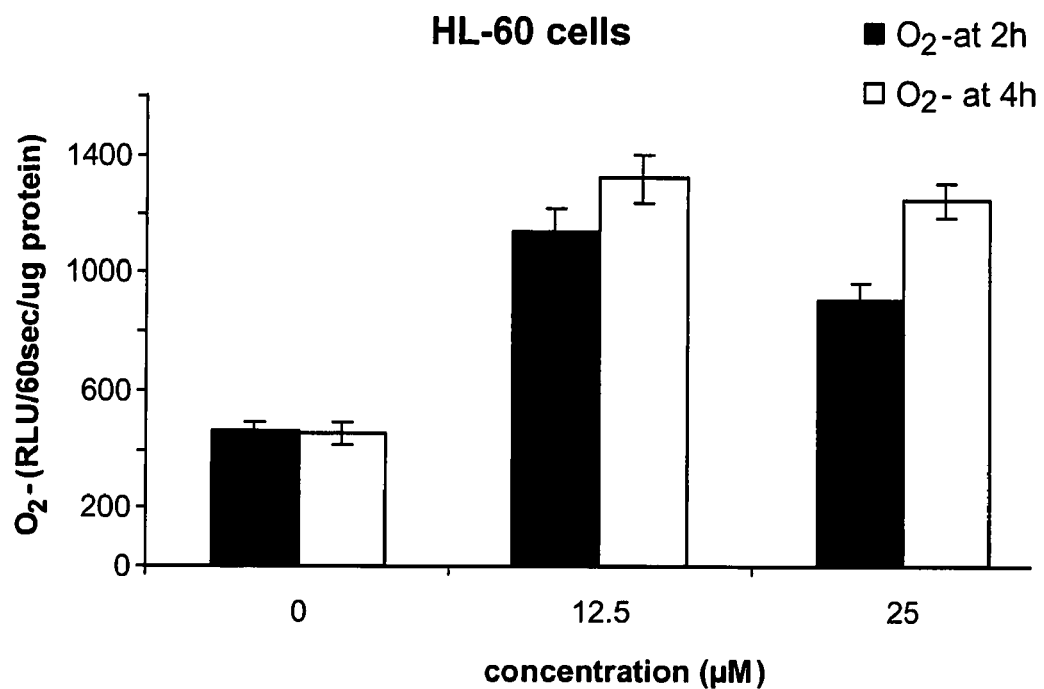
Figure 5C:
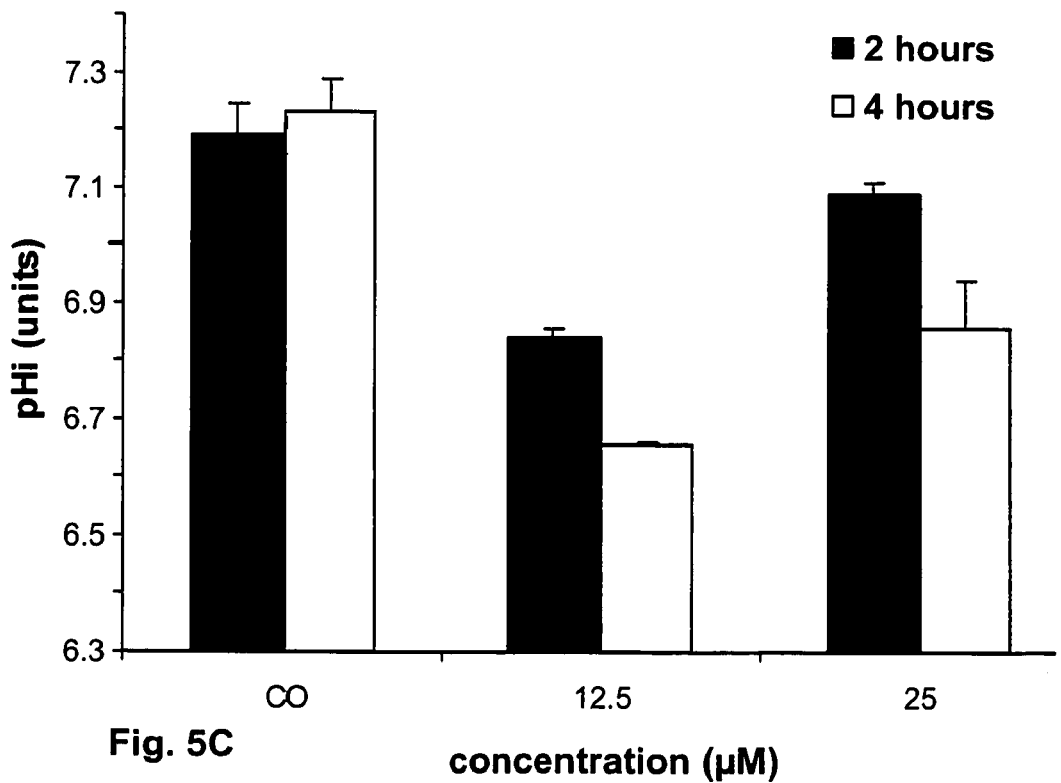
Figure 13:
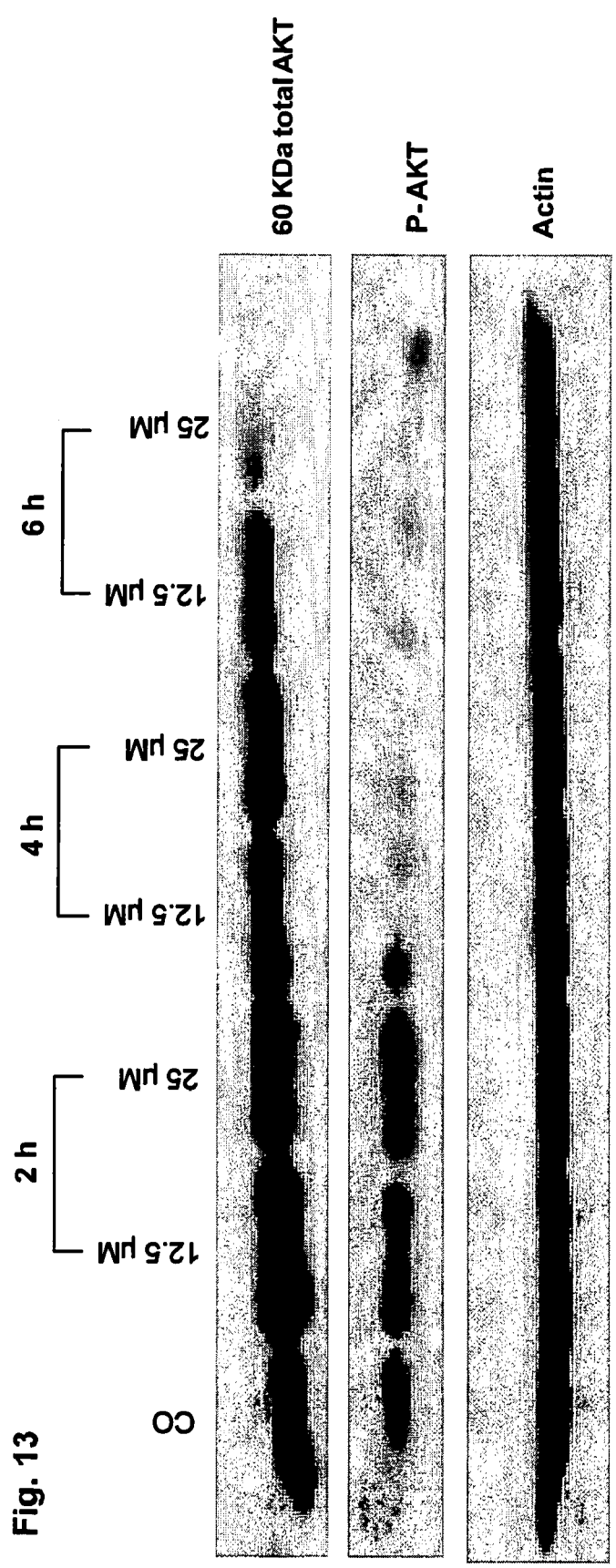
FIG. 13 shows that [Os$_3$(CO)$_{10}$(μ-H)(μ-S)C$_9$H$_6$N] induces down regulation of phospho-AKT. The capability of the varying doses of [Os$_3$(CO)$_{10}$(μ-H)(μ-S)C$_9$H$_6$N] to dephosphorylate and deactivate Akt was shown by Western blot. HL 60 cells (2×10$^6$) were incubated with varying doses of [Os$_3$(CO)$_{10}$(μ-H)(μ-S)C$_9$H$_6$N] (12.5 and 25 μM) for 2, 4, and 6 hours and cell lysates were obtained for Western blot analysis of the Akt phosphorylation status.
Figure 14A:
FIG. 14 depicts the determination of DNA damage by a Comet assay. HL-60 Cells were treated with the concentration of 12.5 uM of [Os$_3$(CO)$_{10}$(μ-H)(μ-S)C$_9$H$_6$N] at 4 hours (B) in comparison to reference cells not exposed to the osmium triangulo compound (A). Cells suspension spreaded on agrose slide and precoated with agrose layer again. After gelling for 5 min at 4° C., the cover slip was gently removed and a third layer of 100 μl of LMA was added and allowed to solidify for 5 min at 4° C. Slides were then placed in a tank filled with the lysis solution (0.03 M NaOH, 1 M NaCl, 0.1% SLS, pH 12.5, at 4° C.) and kept refrigerated for 1 h. The slides were then placed in an electrophoresis tank filled with buffer of 0.075 M NaOH, 2 mM EDTA, pH 12.5 (at room temperature). Electrophoresis was carried out at room temperature for 25 min at 1 V/cm and about 240 mA. Finally, slides were gently washed twice in ultra pure water. And stained with acridine orange (100 μg/ml in water, 50 μl/slide), and read with a cube U-MWB (excitation filter 450-480 nm, barrier filter 515 nm). Tail measurement was done with reference as a control (FIG. 14 A).
Figure 14B:
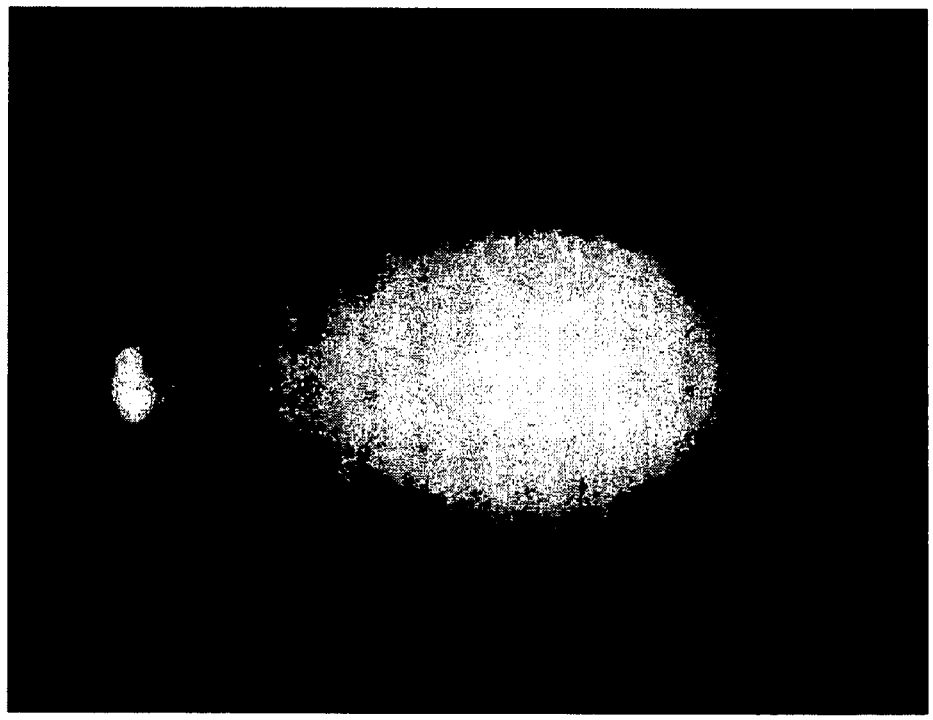

Data are shown in FIG. 5 and FIG. 6. An early increase in intracellular $O_2$ was detected in cells upon exposure to the Os cluster compound (FIG. 5A, B), together with a significant drop in cytosolic pH (FIG. 5C).

Flow Cytometric Analysis of Intracellular $H_2O_2$ Concentration

This example illustrates determining the effect of an osmium triangulo compound of the invention on cellular redox status. The effect on intracellular $H_2O_2$ production is measured for this purpose.

Intracellular $H_2O_2$ was determined by staining with 2,7-dichloro-fluorescein diacetate (Molecular Probes, Eugene, Oreg.), which is oxidised to dichlorofluorescein by $H_2O_2$ described elsewhere (Hirpara, J. L., et al., *J Biol. Chem.* (2001) 276, 514-521). In brief, HL-60 cells were exposed to 12.5 and 25 mM $[Os_3(CO)_{10}(\mu\text{-H})(\mu\text{-S})C_9H_6N]$ 4 h, loaded with 20 mM 2',7'-dichlorofluorescein diacetate at 37° C. for 30 mM, and analysed by flow cytometry (Coulter Epics Elite ESP; excitation 488 nm). Catalase (1000 units/ml) was used to scavenge intracellular $H_2O_2$ before addition of the drugs and flow cytometric analysis of $H_2O_2$ for 4 h, followed by flow cytometry for $H_2O_2$. At least 10,000 events were analysed.

Results are depicted in FIG. 6. Exposure of tumour cells to the Os cluster compound (12.5 mM and 25 mM) resulted in a significant surge in intracellular $H_2O_2$ within 4 hours of treatment, which could be completely blocked by the $H_2O_2$ scavenger catalase (1000 U/ml) (FIG. 6).

It can furthermore be verified whether the measurement of an increase in intracellular ROS production following exposure to the Os cluster compound was a function of intracellular ROS production or a non-specific increase due to interaction of the compound with components present in the culture medium (extracellular). To do so, the culture medium was incubated in the absence of cells with $[Os_3(CO)_{10}(\mu\text{-H})(\mu\text{-S})C_9H_6N]$ (12.5 mM and 25 mM) in the presence or absence of the sensitive probe DCHF-DA, and $H_2O_2$ production was monitored by the increase in fluorescence using a spectrofluorometer. There was no significant increase in DCF fluorescence under these conditions (FIG. 7), thus indicating that $H_2O_2$ produced upon exposure to $[Os_3(CO)_{10}(\mu\text{-H})(\mu\text{-S})C_9H_6N]$ was a function of intracellular activation of ROS production and not a non-specific reaction of the drug with components in the culture medium.

Determination of Caspases Activities

Caspases 2, 3, 8, and 9 activities were assayed by using AFC-conjugated substrates supplied by Bio-Rad. Cells ($1 \times 10^6$ cells/ml) were incubated with the drugs over a time course, washed twice with 1×PBS, resuspended in 50 µl of chilled cell lysis buffer (provided by the supplier), and incubated on ice for 10 min. 50 µl of 2× reaction buffer (10 mM HEPES, 2 mM EDTA, 10 mM KCl, 1.5 mM $MgCl_2$, 10 mM dithiothreitol) and 6 ml of the fluorogenic caspase-specific (VDVAD-AFC for caspase 2, DEVD-AFC for caspase 3, IETD-AFC for caspase 8, and LEHDAFC for caspase 9) were added to each sample and incubated at 37° C. for 1 h. Protease activity was determined by the relative fluorescence intensity at 505 nm following excitation at 400 nm using a spectrofluorimeter (Luminescence Spectrometer LS50B, PerkinElmer Life Sciences, Buckinghamshire, United Kingdom).

Treatment of tumour cells for 12 hours with $[Os_3(CO)_{10}(\mu\text{-H})(\mu\text{-S})C_9H_6N]$ resulted in a significant increase in the surface expression of the death receptor CD95 (FIG. 8).

CD95 signaling is dependent upon the recruitment of Death Inducing Signaling Complex (DISC) thereby bringing about cleavage/activation of the apical caspase, caspase 815, which in turn facilitates downstream caspase cascade involving active caspase 9, caspase-3, and caspase-6. Exposure of tumour cells to $[Os_3(CO)_{10}(\mu\text{-H})(\mu\text{-S})C_9H_6N]$ resulted in activation of caspases (caspases 2, 8, 9, and 3) within 6 hours in both HL60 and Jurkat cells, with the activities being more pronounced in HL60 cells (FIG. 9 A, B). In addition, western blot analyses of the pro-caspase and cleaved products were carried out to obtain direct

Determination of Mitochondrial Trans-Membrane Potential ($\Delta\Psi_m$) by Flow Cytometry Potential-sensitive probe 3,3' dihexyloxacarbocyanine iodide ($DiOC_6$) was used to measure mitochondrial $\Delta\Psi_m$ as described previously (Pervaiz, S., et al., Blood (1999) 93, 12, 4096-4108, incorporated herein by reference in its entirety). Mitochondria were isolated from rat liver (Albino rats, Wistar strain), as described previously (Pervaiz et al., 1999, supra). Briefly, liver cells were homogenised in 10 mL of buffer A (0.3 mol/L sucrose, 5 mmol/L TES, 0.2 mmol/L EGTA, pH 7.2, with KOH) and centrifuged at 2,000 g for 10 minutes at 4° C. The supernatant (S1) was removed and the pellet was resuspended in 10 mL of a buffer of 0.3 mol/L sucrose, 5 mmol/L TES, 0.2 mmol/L EGTA, pH 7.2, with KOH, and centrifuged at 2,000 g for 10 minutes at 4° C. The supernatant obtained (S2) was then mixed with S1 and centrifuged at 8,000 g for 10 minutes at 4° C. The pellet was then resuspended in 1 mL of buffer A, loaded on top of a percoll gradient (60%, 30%, 18%) prepared in above buffer (0.3 mol/L sucrose, 5 mmol/L TES, 0.2 mmol/L EGTA, pH 7.2), and centrifuged at 8,000 g for 10 minutes at 4° C. Mitochondria were then separated from nonmitochondrial membranes and nonfunctional organelles, collected at the 30%/60% interface, and washed with 10 vol of above buffer (0.3 mol/L sucrose, 5 mmol/L TES, 0.2 mmol/L EGTA, pH 7.2) at 8,000 g for 10 minutes at 4° C. to wash off the percoll. Mitochondria were then resuspended in 2 mL of above buffer (0.3 mol/L sucrose, 5 mmol/L TES, 0.2 mmol/L EGTA, pH 7.2, with KOH) and kept at 4° C. with gentle stirring. All experiments with isolated mitochondria were performed within 4 hours of the preparation.

Fifty micrograms purified rat liver mitochondria were incubated for 15 minutes at 37° C. with 40 nmol/L $DiOC_6$. After two gentle washes with 1×PBS, mitochondria were analysed in an Epics Profile (Coulter, Hialeah, Fla.) flow cytometer with the excitation set at 488 nm. At least 10,000 events were collected per sample and data were analyzed by the WINMDI software.

Similarly, $1 \times 10^6$ cells were incubated with 3,3' DiOC6 (40 nM) for 15 min at 37° C. Cells were washed twice with 1×PBS and immediately analysed in Epic Profile flow cytometer with excitation set at 488 nm. Data were analysed for 10,000 events using the WinMDI software.

Confocal Microscopy

Cells were added with 4% (v/v) paraformaldehyde to fix the cells and incubated for 30 mins at −20° C. The cells were washed thrice in ice-cold 1×PBS to remove excess paraformaldehyde, before being subjected to 0.2% (v/v) Triton X-100 for 10 mins at RT to facilitate the permeabilization of the cells. The fixed and permeabilised cells were then washed thrice with ice-cold 1×PBS before being blocked with 1% (w/v) BSA in 1×PBS for 30 mins at 37° C. The cells were again washed three times to remove excess blocking buffer. Primary mouse monoclonal antibody (Molecular Probes, Oreg., USA) and primary rabbit polyclonal bax antibody (Santa Cruz, Calif., USA) in blocking buffer (1% (w/v) BSA and 1×PBS) were added to HL-60 cell lines at 1:1000 dilution. The cells were incubated for 1 h at RT. Following which, the cells were washed three times with ice-cold 1×PBS to remove excess unbound primary antibodies before being added with goat anti-mouse Texas Red-conjugated secondary antibody (Molecular Probes, Oreg., USA) and goat anti-rabbit FITC-conjugated secondary antibody (DakoCytomation, Calif., USA). The cells were incubated for 1 h at RT and washed three times with ice-cold 1×PBS to remove excess unbound secondary fluorescent antibodies. The cells were then mounted onto a microscope glass slide (Livingstone, NSW, Australia) with 10 µl of Vectorshield. The fluorochromes were subjected to excitation wavelengths of 488 nm at 1 mW HeNe Green and 543 nm at 40 mW Argon for FITC and Texas Red respectively using an Olympus IX81 FluoView™ 500 confocal microscope (NY, USA).

Western blotting for Cytochrome C

Cytochrome c release was assessed by Western blot analysis of cytosolic extracts from $30 \times 10^6$ cells as described previously (Hirpara, J. L. et al., *J. Biol. Chem.* (2001) 276, 514-521, incorporated herein by reference in its entirety; Pervaiz et al., 1999, supra). Cytosolic fractions were obtained and analysed by Western blotting.

Briefly, cells were washed twice with ice-cold PBS, pH 7.4, followed by centrifugation at 200×g for 5 minutes. The cell pellet was then resuspended in 600 µL of extraction buffer, containing 200 mmol/L mannitol, 68 mmol/L sucrose, 50 mmol/L PIPES-KOH, pH 7.4, 50 mmol/L KCl, 5 mmol/L EGTA, 2 mmol/L $MgCl_2$, 1 mmol/L DTT, and protease inhibitors (Complete Cocktail; Boehringer Mannheim, Mannheim, Germany). After 30 minutes of incubation on ice, cells were homogenised with a dounce homogeniser, the homogenate was spun at 14,000×g for 15 minutes, and supernatants were removed and stored at 80° C. until analysis by gel electrophoresis. Monoclonal anti-Cyt.C antibody (clone 7H, 8.2; C12; Pharmingen, San Diego, Calif.) was used. Signal was detected by the Super Signal Substrate Western Blotting kit (Pierce).

Western Blot Analyses of Poly(ADP-Ribose) Polymerase Cleavage, Bax, and Bid

For analysis of poly(ADP-ribose) polymerase cleavage, lysates from $2\times10^6$ cells were prepared in sample buffer [50 mmol/L Tris/HCl (pH 6.8), 6 mol/L urea, 3% SDS, 0.003% Bromphenol Blue, and 6% β-mercaptoethanol] and subjected to Western blot analysis using anti-poly(ADP-ribose) polymerase (clone C-2-10, PharMingen) as described (Pervaiz et al., 199, supra). For Western blot analysis of Bax, cells ($2\times10^6$) were lysed by adding 100 ml of chilled 1× radioimmunoprecipitation assay buffer lysis buffer, and 50 µg of protein were subjected to 15% PAGE and transferred to polyvinylidene difluoride as above. Alternatively for analysis of Bax dimerization/multimerization, cell lysates were subjected to 10% native gel electrophoresis. Membranes were exposed to 1:2,000 dilution of mouse monoclonal anti-Bax antibody (clone 6A7, BD Pharmigen, San Diego, Calif.) at 25° C. for 2 hours, followed by 1:5,000 dilution of goat antimouse IgG-horseradish peroxidase. The anti-Bax antibody (6A7) recognises epitopes that are in the vicinity of the dimerization domains of Bax. Western blot analysis for Bid cleavage was performed on whole cell lysates using a rabbit polyclonal anti-Bid IgG (Biovision Research Products, Paolo Alto, Calif.) that recognises the Mr 22,000 full-length Bid. Chemiluminescence was detected as described above.

Data depicted in FIG. 10 show that overexpression of Bcl-2 blocked $[Os_3(CO)_{10}(\mu\text{-H})(\mu\text{-S})C_9H_9N]$-induced apoptosis. Of note, while cytochrome C release occurred in a dose dependent manner upon exposure to $[Os_3(CO)_{10}(\mu\text{-H})(\mu\text{-S})C_9H_6N]$ (FIG. 11A), there was no significant change in the sub-cellular localization of Bax (FIG. 11B).

Detection of Total Akt/Protein Kinase B and Akt/Protein Kinase B Phosphorylation Levels HL-60 cells ($2\times10^6$) were plated in a 12 well plate followed by exposure to the drug. Cells were harvested, washed once with PBS, and then lysed with cell lysis buffer [150 mmol/L NaCl, Tris-HCl (pH 7.4), 1% NP40]. Cell lysate (200 µg) was then electrophoresed on an 8% acrylamide gel. Antibodies were used to probe for total Akt and phosphorylated Akt/PKB at the Ser473 position (Cell Signaling, Beverly, Mass.). Protein blots were probed with anti β-actin (Sigma-Aldrich, St. Louis, Mo.) to check for equal protein loading).

FIG. 11C depicts data on the effect of $[Os_3(CO)_{10}(\mu\text{-H})(\mu\text{-S})C_9H_6N]$ on the activation of the survival kinase, Akt/PKB. Interestingly, while the total Akt signal remained almost unchanged (see FIG. 11C, upper pannel), there was a strong inhibition of Akt phosphorylation within 4 to 6 hours of exposure (see FIG. 11C, middle pannel). These data provide evidence that $[Os_3(CO)_{10}(\mu\text{-H})(\mu\text{-S})C_9H_6N]$ in addition to inducing apoptotic cell death, also targeted the PI3K/Akt survival pathway, which could have tremendous clinical implications.

DNA Damage Measurement by Comet Assay

The comet assay was done as described elsewhere (Choucroun, P., et al. *Mutation Research/Fundamental and Molecular Mechanisms of Mutagenesis* (2001) 478, 89-96, incorporated herein by reference in its entirety). In brief, in the week before each experiment, frosted microscope slides were cleaned, dried with alcohol, and precoated with two thin layers of normal melting agarose (0.6% in ultra pure water), left at room temperature to allow agarose to dry, then kept refrigerated at 4° C.

Every 30 or 60 min after apoptosis induction (a control was taken immediately before induction), an aliquot of 15 µl of cell suspension was taken and suspended in 200 µl of low melting agarose (0.8% in Dulbecco's phosphate buffer saline) at 37° C. An amount of 75 µl of this agarose cell suspension was spread on each of two precoated slides and covered with a coverslip. After gelling for 5 min at 4° C., the cover slip was gently removed and a third layer of 100 µl of low melting agarose was added and allowed to solidify for 5 min at 4° C. Slides were then placed in a tank filled with the lysis solution (0.03 M NaOH, 1 M NaCl, 0.1% SLS, pH 12.5, at 4° C.) and kept refrigerated for 1 h. Then, slides were removed from the lysis solution and transferred into a tank containing unwinding solution (0.3 M NaOH, 2 mM EDTA, pH 13, at 4° C.). The tank was kept at 4° C. for 30 min. The slides were then put in an electrophoresis tank filled with the buffer (0.075 M NaOH, 2 mM EDTA, pH 12.5, at room temperature). Electrophoresis was carried out at room temperature for 25 min at 1 V/cm and about 240 mA. Finally, slides were gently washed twice in ultra pure water. Slide reading was performed immediately with an Olympus epifluorescence microscope BX-40 and a cube U-MWG (excitation filter 510-550 nm, barrier filter 590 nm), at 200× magnification, after staining with ethidium bromide solution (20 µg/ml, 50 µl/slide). For each slide, 50 randomly selected cells were analyzed both visually and with the image analysis system comet 3.1 (Kinetic Imaging). Some slides were stained with acridine orange (100 µg/ml in water, 50 µl/slide), and read with a cube U-MWB (excitation filter 450-480 nm, barrier filter 515 nm).

The listing or discussion of a previously published document in this specification should not necessarily be taken as an acknowledgement that the document is part of the state of the art or is common general knowledge. All documents listed are hereby incorporated herein by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognise that the invention is also thereby described in terms of any individual member or subgroup of members of the Markush group.

What is claimed is:

1. A metal triangulo compound of the general formula (I)

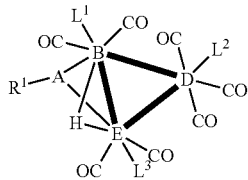

wherein:
$R^1$ is quinoline,
A is selected from the group consisting of S, Se, $PO_4$, $PO_3(R^2)$ and $P—(R^2)_3$, wherein $R^2$ is selected from the group consisting of H, aliphatic, cycloaliphatic, aromatic, arylaliphatic, and arylcycloaliphatic groups, comprising 0-6 heteroatoms selected from the group N, O, S, Se and Si,
$L^1$, $L^2$ and $L^3$ are ligands independently selected from the group consisting of —CO, —$NC(R^2)$, CN—$R^2$ and —$P—(R^2)_3$,
wherein $R^2$ is H or selected from the group consisting of aliphatic, cycloaliphatic, aromatic, arylaliphatic, and arylcycloaliphatic groups, comprising 0-6 heteroatoms selected from the group N, O, S, Se and Si, and
B, D and E are independently selected from the group consisting of osmium, ruthenium, rhenium, rhodium, iridium and tin.

2. The metal triangulo compound of claim 1, wherein B, D and E are identical.

3. The metal triangulo compound of claim 1, wherein $L^1$, $L^2$ and $L^3$ are CO.

4. The method of forming a metal triangulo compound according to claim 1, said method comprising contacting a compound of formula (III)

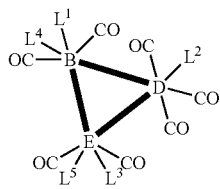

with a compound of general formula R1-AH,
wherein:
B, D and E are independently selected from the group consisting of osmium, ruthenium, rhenium, rhodium, iridium and tin,
$L^1$, $L^2$ and $L^3$ are ligands independently selected from the group consisting of CO, —$NC(R^2)$, CN—$R^2$ and —$P—(R^2)_3$,
wherein $R^2$ is H or selected from the group consisting of aliphatic, cycloaliphatic, aromatic, arylaliphatic, and arylcycloaliphatic groups, comprising 0-6 heteroatoms selected from the group N, O, S, Se and Si,
$L^4$ and $L^5$ are independently selected from the group consisting of NC—$CH_3$, CO, NO and H, $R^1$ is quinoline, and
A is selected from the group consisting of S, Se, $PO_4$, $PO_3(R^2)$ and $P—(R^2)_3$,
wherein $R^2$ is H or selected from the group consisting of H, aliphatic, cycloaliphatic, aromatic, arylaliphatic, and arylcycloaliphatic groups, comprising 0-6 heteroatoms selected from the group N, O, S, Se and Si.

5. The method of claim 4, wherein said compound of general formula (III) is of general formula (IV):

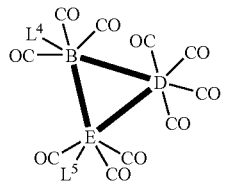

and wherein the method comprises forming a compound of general formula (V):

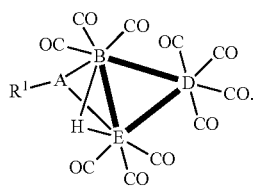

6. The method of claim 5, wherein the compound of formula (IV) is bis(acetonitrile)decacarbonyltriosmium.

7. A method of inducing apoptosis in a leukemia cell comprising administering a metal triangulo compound of formula (I)

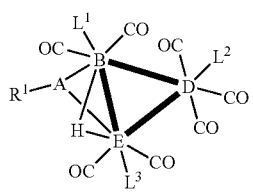

wherein:
$R^1$ is quinoline,
A is selected from the group consisting of S, Se, $PO_4$, $PO_3(R^2)$ and $P—(R^2)_3$,
wherein $R^2$ is selected from the group consisting of H, aliphatic, cycloaliphatic, aromatic, arylaliphatic, and arylcycloaliphatic groups, comprising 0-6 heteroatoms selected from the group N, O, S, Se and Si,
$L^1$, $L^2$ and $L^3$ are ligands independently selected from the group consisting of —CO, —$NC(R^2)$, CN—$R^2$ and —$P—(R^2)_3$,
wherein $R^2$ is H or selected from the group consisting of aliphatic, cycloaliphatic, aromatic, arylaliphatic, and arylcycloaliphatic groups, comprising 0-6 heteroatoms selected from the group N, O, S, Se and Si, and
B, D and E are independently selected from the group consisting of osmium, ruthenium, rhenium, rhodium, iridium and tin.

8. A method of treating carcinogenesis in a leukemia cell comprising administering a metal triangulo compound of formula (I)

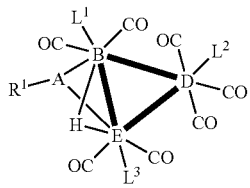

wherein:

$R^1$ is quinoline,

A is selected from the group consisting of S, Se, $PO_4$, $PO_3(R^2)$ and P—$(R^2)_3$, wherein $R^2$ is selected from the group consisting of H, aliphatic, cycloaliphatic, aromatic, arylaliphatic, and arylcycloaliphatic groups, comprising 0-6 heteroatoms selected from the group N, O, S, Se and Si, $L^1$, $L^2$ and $L^3$ are ligands independently selected from the group consisting of —CO, —NC($R^2$), CN—$R^2$ and —P—$(R^2)_3$, wherein $R^2$ is H or selected from the group consisting of aliphatic, cycloaliphatic, aromatic, arylaliphatic, and arylcycloaliphatic groups, comprising 0-6 heteroatoms selected from the group N, O, S, Se and Si, and B, D and E are independently selected from the group consisting of osmium, ruthenium, rhenium, rhodium, iridium and tin.

9. A pharmaceutical composition, comprising (a) a metal triangulo compound of formula (I),

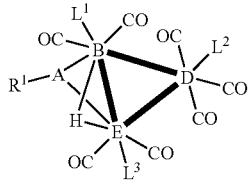

wherein:

$R^1$ is quinoline,

A is selected from the group consisting of S, Se, $PO_4$, $PO_3(R^2)$ and P—$(R^2)_3$, wherein $R^2$ is selected from the group consisting of H, aliphatic, cycloaliphatic, aromatic, arylaliphatic, and arylcycloaliphatic groups, comprising 0-6 heteroatoms selected from the group N, O, S, Se and Si, $L^1$, $L^2$ and $L^3$ are ligands independently selected from the group consisting of —CO, —NC($R^2$), CN—$R^2$ and —P—$(R^2)_3$, wherein $R^2$ is H or selected from the group consisting of aliphatic, cycloaliphatic, aromatic, arylaliphatic, and arylcycloaliphatic groups, comprising 0-6 heteroatoms selected from the group N, O, S, Se and Si, and B, D and E are independently selected from the group consisting of osmium, ruthenium, rhenium, rhodium, iridium and tin, and (b) a carrier or diluent, for inducing apoptosis in a leukemia cell and/or treating carcinogenesis in a leukemia cell.

10. The pharmaceutical composition of claim 9, further comprising at least one of a nucleic acid alkylator, a nucleoside analogue, an anthracycline, an antibiotic, an aromatase inhibitor, a folate antagonist, an estrogen receptor modulator, an inorganic aresenate, a microtubule inhibitor, a nitrosourea, an osteoclast inhibitor, a platinum containing compound, a retinoid, a topoisomerase 1 inhibitor, a topoisomerase 2 inhibitor, a thymidylate synthase inhibitor, an aromatase inhibitor, a cyclo-oxygenase inhibitor, an isoflavone, a tyrosine kinase inhibitor, a growth factor, a bisphosphonate, and a monoclonal antibody.

\* \* \* \* \*

UNITED STATES PATENT AND TRADEMARK OFFICE
CERTIFICATE OF CORRECTION

PATENT NO. : 8,399,447 B2  Page 1 of 1
APPLICATION NO. : 12/596138
DATED : March 19, 2013
INVENTOR(S) : Pervaiz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 657 days.

Signed and Sealed this
First Day of September, 2015

Michelle K. Lee
*Director of the United States Patent and Trademark Office*